US008247621B2

(12) United States Patent
Ritter et al.

(10) Patent No.: US 8,247,621 B2
(45) Date of Patent: Aug. 21, 2012

(54) PROCESS FOR MAKING 2-SECONDARY-ALKYL-4,5-DI-(NORMAL-ALKYL)PHENOLS

(75) Inventors: Joachim C. Ritter, Wilmington, DE (US); James Michael Garner, Wilmington, DE (US)

(73) Assignee: Invista North America S.A.R.L., Wilmington, DE (US)

( * ) Notice: Subject to any disclaimer, the term of this patent is extended or adjusted under 35 U.S.C. 154(b) by 299 days.

(21) Appl. No.: 12/577,258

(22) Filed: Oct. 12, 2009

(65) Prior Publication Data

US 2010/0099922 A1 Apr. 22, 2010

Related U.S. Application Data

(60) Provisional application No. 61/105,185, filed on Oct. 14, 2008.

(51) Int. Cl.
*C07C 37/14* (2006.01)
(52) U.S. Cl. ........ 568/790; 568/791; 568/792; 568/793; 568/794
(58) Field of Classification Search .................. None
See application file for complete search history.

(56) References Cited

U.S. PATENT DOCUMENTS

| 2,768,132 | A | 10/1956 | Halliwell |
| 3,037,052 | A | 5/1962 | Bortnick |
| 3,370,082 | A | 2/1968 | Eisfeld et al. |
| 3,496,215 | A | 2/1970 | Drinkard et al. |
| 3,496,217 | A | 2/1970 | Drinkard, Jr. et al. |
| 3,496,218 | A | 2/1970 | Drinkard, Jr. |
| 3,522,288 | A | 7/1970 | Drinkard, Jr. et al. |
| 3,536,748 | A | 10/1970 | Drinkard, Jr. et al. |
| 3,551,474 | A | 12/1970 | Drinkard et al. |
| 3,564,040 | A | 2/1971 | Downing et al. |
| 3,579,560 | A | 5/1971 | Drinkard et al. |
| 3,655,723 | A | 4/1972 | Drinkard, Jr. et al. |
| 3,694,485 | A | 9/1972 | Drinkard, Jr. et al. |
| 3,752,839 | A | 8/1973 | Drinkard, Jr. et al. |
| 3,766,231 | A | 10/1973 | Gosser et al. |
| 3,766,237 | A | 10/1973 | Chia et al. |
| 3,766,241 | A | 10/1973 | Drinkard, Jr. et al. |
| 3,773,809 | A | 11/1973 | Walter |
| 3,775,461 | A | 11/1973 | Drinkard, Jr. et al. |
| 3,798,256 | A | 3/1974 | King et al. |
| 3,818,067 | A | 6/1974 | Downing et al. |
| 3,818,068 | A | 6/1974 | Wells |
| 3,846,474 | A | 11/1974 | Mok |
| 3,849,472 | A | 11/1974 | Waddan |
| 3,850,973 | A | 11/1974 | Seidel et al. |
| 3,853,754 | A | 12/1974 | Gosser |
| 3,853,948 | A | 12/1974 | Drinkard, Jr. et al. |
| 3,864,380 | A | 2/1975 | King et al. |
| 3,869,501 | A | 3/1975 | Waddan |
| 3,920,721 | A | 11/1975 | Gosser |
| 3,927,056 | A | 12/1975 | Gosser |
| 3,947,487 | A | 3/1976 | Crooks |
| 4,045,495 | A | 8/1977 | Nazarenko et al. |
| 4,046,815 | A | 9/1977 | Nazarenko |
| 4,076,756 | A | 2/1978 | Nazarenko et al. |
| 4,087,452 | A | 5/1978 | Kuntz |
| 4,146,555 | A | 3/1979 | Kershaw |
| 4,147,717 | A | 4/1979 | Kershaw |
| 4,177,215 | A | 12/1979 | Seidel |
| 4,198,531 | A * | 4/1980 | Merger et al. ............... 568/793 |
| 4,210,558 | A | 7/1980 | Crooks |
| 4,230,634 | A | 10/1980 | Benzie et al. |
| 4,236,031 | A | 11/1980 | Dodd |
| 4,236,032 | A * | 11/1980 | Dodd ........................... 568/788 |
| 4,240,976 | A | 12/1980 | Benzie et al. |
| 4,251,468 | A | 2/1981 | Nazarenko |
| 4,328,172 | A | 5/1982 | Rapoport |
| 4,330,483 | A | 5/1982 | Rapoport |
| 4,339,395 | A | 7/1982 | Barnette et al. |
| 4,371,474 | A | 2/1983 | Rapoport |
| 4,380,677 | A | 4/1983 | Kurek |
| 4,382,038 | A | 5/1983 | McGill |
| 4,385,007 | A | 5/1983 | Shook, Jr. |
| 4,416,824 | A | 11/1983 | Reimer et al. |
| 4,416,825 | A | 11/1983 | Ostermaier |
| 4,434,316 | A | 2/1984 | Barnette |
| 4,539,302 | A | 9/1985 | Leyendecker et al. |
| 4,705,881 | A | 11/1987 | Rapoport |
| 4,749,801 | A | 6/1988 | Beatty et al. |
| 4,774,353 | A | 9/1988 | Hall et al. |
| 4,874,884 | A | 10/1989 | McKinney et al. |
| 4,990,645 | A | 2/1991 | Back et al. |
| 5,107,012 | A | 4/1992 | Grunewald |
| 5,208,390 | A * | 5/1993 | Onopchenko et al. ........ 568/766 |
| 5,235,113 | A | 8/1993 | Sato et al. |

(Continued)

FOREIGN PATENT DOCUMENTS

AU 6522096 2/1997

(Continued)

OTHER PUBLICATIONS

Kunin et al., I&EC Product Research and Development (1962), 1(2), p. 140-144.*
Houben-Weyl, vol. 6/1C, pp. 955-985, G. Thieme Verlag, Stuttgart 1976.
J. Kamis, Collection of Czechoslovak Chemical Communications, 1964, 29(12), pp. 3176-3178.
S. P. Starkov and L. V. Glushkova, Journal of Applied Chemistry of the USSR, 1967, 40, pp. 209-211.
S. P. Starkov and L. V. Glushkova, Journal of Applied Chemistry of the USSR, 1967, 40, pp. 1583-1584.
Tetrahedron Letters, 1994, 35, pp. 7983-7984.

*Primary Examiner* — Brian J Davis
(74) *Attorney, Agent, or Firm* — Robert B. Furr, Jr.

(57) ABSTRACT

The invention relates to the preparation of alkylated phenols. More specifically, the invention relates to an improved process for the manufacture of 2-secondary-alkyl-4,5-di-normal-alkylphenols.

31 Claims, 3 Drawing Sheets

U.S. PATENT DOCUMENTS

Figure 1:
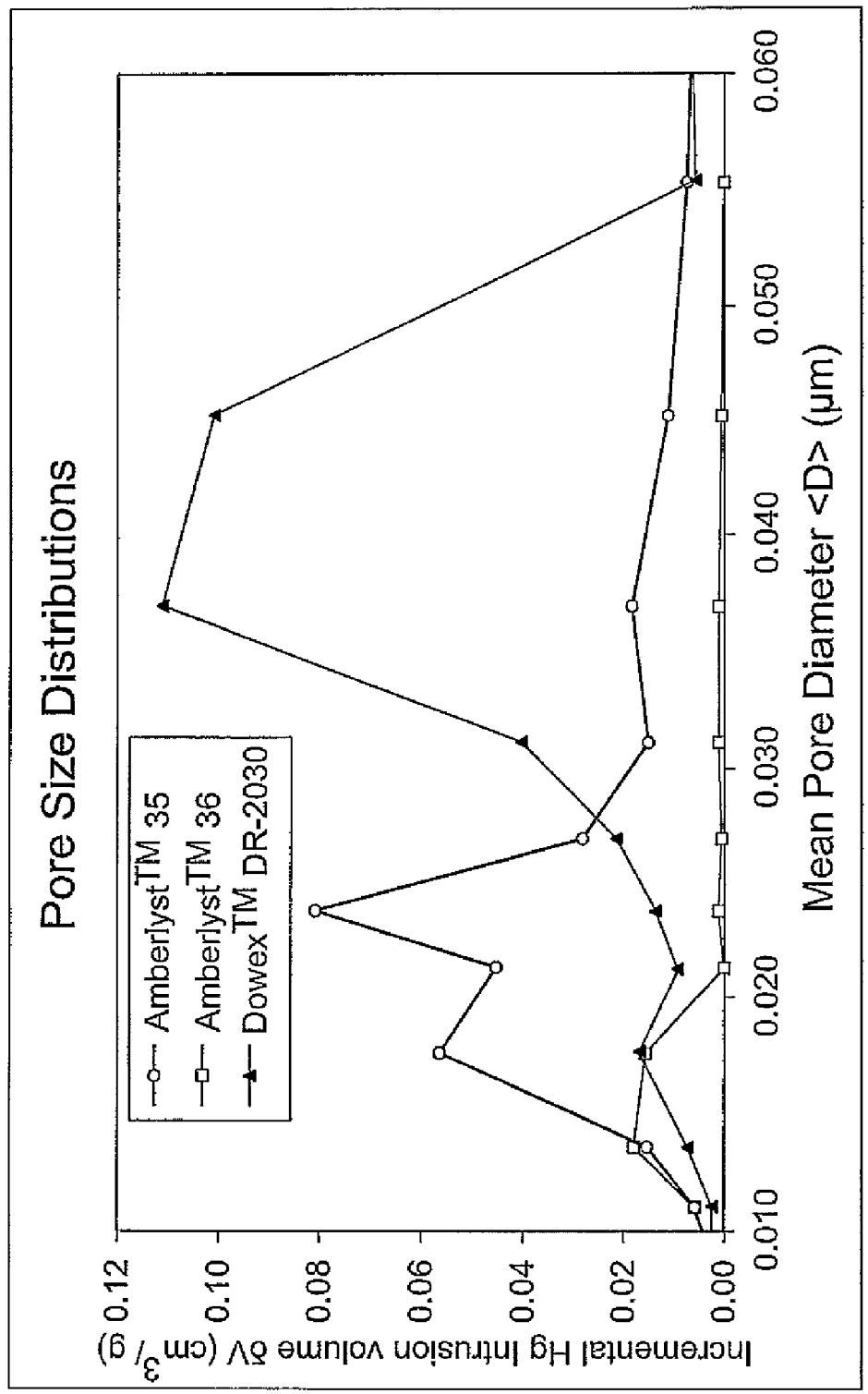

| | | | |
|---|---|---|---|
| 5,302,756 A | 4/1994 | McKinney | |
| 5,312,959 A | 5/1994 | Sieja et al. | |
| 5,449,807 A | 9/1995 | Druliner | |
| 5,488,129 A | 1/1996 | Huser et al. | |
| 5,512,695 A | 4/1996 | Kreutzer et al. | |
| 5,512,696 A | 4/1996 | Kreutzer et al. | |
| 5,523,453 A | 6/1996 | Breikss | |
| 5,543,536 A | 8/1996 | Tam | |
| 5,663,369 A | 9/1997 | Kreutzer et al. | |
| 5,688,986 A | 11/1997 | Tam | |
| 5,696,280 A | 12/1997 | Shapiro | |
| 5,709,841 A | 1/1998 | Reimer | |
| 5,723,641 A | 3/1998 | Tam et al. | |
| 5,773,637 A | 6/1998 | Cicha et al. | |
| 5,821,378 A | 10/1998 | Foo et al. | |
| 5,847,191 A | 12/1998 | Bunel et al. | |
| 5,856,555 A | 1/1999 | Huser et al. | |
| 5,908,805 A | 6/1999 | Huser et al. | |
| 5,959,135 A | 9/1999 | Garner et al. | |
| 6,031,120 A | 2/2000 | Tam | |
| 6,069,267 A | 5/2000 | Tam | |
| 6,090,987 A | 7/2000 | Billig et al. | |
| 6,121,184 A | 9/2000 | Druliner et al. | |
| 6,147,247 A | 11/2000 | Voit et al. | |
| 6,169,198 B1 | 1/2001 | Fischer et al. | |
| 6,171,996 B1 | 1/2001 | Garner et al. | |
| 6,197,992 B1 | 3/2001 | Fischer et al. | |
| 6,242,633 B1 | 6/2001 | Fischer et al. | |
| 6,284,865 B1 | 9/2001 | Tam et al. | |
| 6,307,109 B1 | 10/2001 | Kanel et al. | |
| 6,355,833 B2 | 3/2002 | Fischer et al. | |
| 6,461,481 B1 | 10/2002 | Barnette et al. | |
| 6,469,194 B2 | 10/2002 | Burattin et al. | |
| 6,521,778 B1 | 2/2003 | Fischer et al. | |
| 6,646,148 B1 | 11/2003 | Kreutzer | |
| 6,660,877 B2 | 12/2003 | Lenges et al. | |
| 6,670,513 B1 * | 12/2003 | Campbell et al. | 568/793 |
| 6,737,539 B2 | 5/2004 | Lenges et al. | |
| 6,753,440 B2 | 6/2004 | Druliner et al. | |
| 6,770,770 B1 | 8/2004 | Baumann et al. | |
| 6,846,945 B2 | 1/2005 | Lenges et al. | |
| 6,852,199 B2 | 2/2005 | Jungkamp et al. | |
| 6,855,799 B2 | 2/2005 | Tam et al. | |
| 6,897,329 B2 | 5/2005 | Jackson et al. | |
| 6,984,604 B2 | 1/2006 | Cobb et al. | |
| 7,022,866 B2 | 4/2006 | Bartsch et al. | |
| 7,067,685 B2 | 6/2006 | Bartsch et al. | |
| 7,084,293 B2 | 8/2006 | Rosier et al. | |
| 7,084,294 B2 | 8/2006 | Jungkamp et al. | |
| 7,098,358 B2 | 8/2006 | Burattin et al. | |
| 7,105,696 B2 | 9/2006 | Burattin et al. | |
| 7,253,298 B2 | 8/2007 | Galland et al. | |
| 7,345,006 B2 | 3/2008 | Bartsch et al. | |
| 7,381,845 B2 | 6/2008 | Weiskopf et al. | |
| 7,439,381 B2 | 10/2008 | Jungkamp et al. | |
| 7,442,825 B2 | 10/2008 | Galland et al. | |
| 7,470,805 B2 | 12/2008 | Rosier et al. | |
| 7,521,575 B2 | 4/2009 | Bartsch et al. | |
| 7,528,275 B2 | 5/2009 | Bartsch et al. | |
| 7,538,240 B2 | 5/2009 | Jungkamp et al. | |
| 7,541,486 B2 | 6/2009 | Scheidel et al. | |
| 7,700,795 B2 | 4/2010 | Haderlein et al. | |
| 2003/0100802 A1 | 5/2003 | Shapiro | |
| 2003/0135014 A1 | 7/2003 | Radu et al. | |
| 2003/0212298 A1 | 11/2003 | Brasse et al. | |
| 2004/0063991 A1 | 4/2004 | Burattin et al. | |
| 2004/0176622 A1 | 9/2004 | Bartsch et al. | |
| 2004/0235648 A1 | 11/2004 | Bartsch et al. | |
| 2004/0260112 A1 | 12/2004 | Basset et al. | |
| 2005/0090677 A1 | 4/2005 | Bartsch et al. | |
| 2005/0090678 A1 | 4/2005 | Bartsch et al. | |
| 2005/0247624 A1 | 11/2005 | Jungkamp et al. | |
| 2006/0142609 A1 | 6/2006 | Bourgeois et al. | |
| 2006/0175189 A1 | 8/2006 | Gerber et al. | |
| 2006/0252955 A1 | 11/2006 | Rosier et al. | |
| 2006/0258873 A1 | 11/2006 | Rosier et al. | |
| 2006/0258874 A1 | 11/2006 | Bartsch et al. | |
| 2006/0264651 A1 | 11/2006 | Bartsch et al. | |
| 2007/0060766 A1 | 3/2007 | Bartsch et al. | |
| 2007/0073071 A1 | 3/2007 | Haderlein et al. | |
| 2007/0083057 A1 | 4/2007 | Haderlein et al. | |
| 2007/0088173 A1 | 4/2007 | Haderlein et al. | |
| 2007/0112215 A1 | 5/2007 | Jungkamp et al. | |
| 2007/0155977 A1 | 7/2007 | Jungkamp et al. | |
| 2007/0155978 A1 | 7/2007 | Jungkamp et al. | |
| 2007/0155980 A1 | 7/2007 | Scheidel et al. | |
| 2008/0015378 A1 | 1/2008 | Foo et al. | |
| 2008/0015380 A1 | 1/2008 | Foo et al. | |
| 2008/0015381 A1 | 1/2008 | Foo et al. | |
| 2008/0015382 A1 | 1/2008 | Foo et al. | |
| 2008/0071105 A1 | 3/2008 | Bartsch et al. | |
| 2008/0076944 A1 | 3/2008 | Bartsch et al. | |
| 2008/0083607 A1 | 4/2008 | Deckert et al. | |
| 2008/0221351 A1 | 9/2008 | Bartsch et al. | |
| 2008/0227214 A1 | 9/2008 | Jungkamp et al. | |
| 2008/0227998 A1 | 9/2008 | Scheidel et al. | |
| 2008/0242883 A1 | 10/2008 | Jungkamp et al. | |
| 2008/0242885 A1 | 10/2008 | Jungkamp et al. | |
| 2008/0242886 A1 | 10/2008 | Bartsch et al. | |
| 2008/0275266 A1 | 11/2008 | Bartsch et al. | |
| 2008/0281119 A1 | 11/2008 | Scheidel et al. | |
| 2008/0281120 A1 | 11/2008 | Jungkamp et al. | |
| 2009/0054671 A1 | 2/2009 | Haderlein et al. | |

FOREIGN PATENT DOCUMENTS

| | | |
|---|---|---|
| AU | 199665220 A | 2/1997 |
| CA | 1324613 C | 11/1993 |
| CA | 2462720 A1 | 4/2003 |
| CA | 2552862 A1 | 8/2005 |
| CN | 1113854 A | 12/1995 |
| CN | 1145531 A | 3/1997 |
| CN | 1146166 A | 3/1997 |
| CN | 1146762 A | 4/1997 |
| CN | 1159406 A | 9/1997 |
| CN | 1159799 A | 9/1997 |
| CN | 1163606 A | 10/1997 |
| CN | 1169143 A | 12/1997 |
| CN | 1173935 A | 2/1998 |
| CN | 1179147 A | 4/1998 |
| CN | 1198151 A | 11/1998 |
| CN | 1204111 A | 1/1999 |
| CN | 1206357 A | 1/1999 |
| CN | 1211931 A | 3/1999 |
| CN | 1045591 C | 10/1999 |
| CN | 1236355 A | 11/1999 |
| CN | 1047163 C | 12/1999 |
| CN | 1245489 A | 2/2000 |
| CN | 1247102 A | 3/2000 |
| CN | 1052718 C | 5/2000 |
| CN | 1265094 A | 8/2000 |
| CN | 1266424 A | 9/2000 |
| CN | 1270543 A | 10/2000 |
| CN | 1304334 A | 7/2001 |
| CN | 1069310 C | 8/2001 |
| CN | 1072980 C | 10/2001 |
| CN | 1076342 C | 12/2001 |
| CN | 1327881 A | 12/2001 |
| CN | 1331843 A | 1/2002 |
| CN | 1333745 A | 1/2002 |
| CN | 1082946 C | 4/2002 |
| CN | 1344180 A | 4/2002 |
| CN | 1356335 A | 7/2002 |
| CN | 1387534 A | 12/2002 |
| CN | 1099912 C | 1/2003 |
| CN | 1390241 A | 1/2003 |
| CN | 1103613 C | 3/2003 |
| CN | 1106218 C | 4/2003 |
| CN | 1108643 C | 5/2003 |
| CN | 1427807 A | 7/2003 |
| CN | 1449400 A | 10/2003 |
| CN | 1461295 A | 12/2003 |
| CN | 147510 A | 1/2004 |
| CN | 1141285 C | 3/2004 |
| CN | 1142224 C | 3/2004 |
| CN | 1144781 C | 4/2004 |
| CN | 1487917 A | 4/2004 |
| CN | 1152855 C | 6/2004 |

| | | | | | | |
|---|---|---|---|---|---|---|
| CN | 1535179 | A | 10/2004 | EP | 675871 | B1 | 4/1997 |
| CN | 1564807 | A | 1/2005 | EP | 634395 | B1 | 9/1997 |
| CN | 1568225 | A | 1/2005 | EP | 650959 | B1 | 9/1997 |
| CN | 1568226 | A | 1/2005 | EP | 784610 | B1 | 2/1999 |
| CN | 1617892 | A | 5/2005 | EP | 757672 | B1 | 6/1999 |
| CN | 1617900 | A | 5/2005 | EP | 792259 | B1 | 8/1999 |
| CN | 1212293 | C | 7/2005 | EP | 804412 | B1 | 12/1999 |
| CN | 1639176 | A | 7/2005 | EP | 1000019 | A1 | 5/2000 |
| CN | 1213051 | C | 8/2005 | EP | 1001928 | A1 | 5/2000 |
| CN | 1665776 | A | 9/2005 | EP | 1003716 | A1 | 5/2000 |
| CN | 1670139 | A | 9/2005 | EP | 1019190 | A1 | 7/2000 |
| CN | 1674989 | A | 9/2005 | EP | 755302 | B1 | 10/2000 |
| CN | 1675172 | A | 9/2005 | EP | 929513 | B1 | 4/2001 |
| CN | 1222358 | C | 10/2005 | EP | 881924 | B1 | 5/2001 |
| CN | 1732148 | A | 2/2006 | EP | 854858 | B1 | 6/2001 |
| CN | 1735460 | A | 2/2006 | EP | 815073 | B1 | 7/2001 |
| CN | 1245489 | C | 3/2006 | EP | 1144114 | A3 | 9/2001 |
| CN | 1740183 | A | 3/2006 | EP | 1091804 | B1 | 2/2002 |
| CN | 1745062 | A | 3/2006 | EP | 944585 | B1 | 4/2002 |
| CN | 1767895 | A | 5/2006 | EP | 1000019 | B1 | 2/2003 |
| CN | 1260009 | C | 6/2006 | EP | 911339 | B1 | 4/2003 |
| CN | 1266424 | C | 7/2006 | EP | 1216268 | B1 | 11/2003 |
| CN | 1270543 | C | 8/2006 | EP | 1350788 | A3 | 11/2003 |
| CN | 1274671 | C | 9/2006 | EP | 1003607 | B1 | 12/2003 |
| CN | 1274699 | C | 9/2006 | EP | 1003716 | B1 | 2/2004 |
| CN | 1835915 | A | 9/2006 | EP | 1313743 | B1 | 3/2004 |
| CN | 1279088 | C | 10/2006 | EP | 1414567 | A1 | 5/2004 |
| CN | 1847288 | A | 10/2006 | EP | 1427695 | A1 | 6/2004 |
| CN | 1283620 | C | 11/2006 | EP | 1438133 | A1 | 7/2004 |
| CN | 1857775 | A | 11/2006 | EP | 1019190 | B1 | 12/2004 |
| CN | 1289539 | C | 12/2006 | EP | 1140801 | B1 | 2/2005 |
| CN | 1293942 | C | 1/2007 | EP | 1395547 | B1 | 3/2005 |
| CN | 1906150 | A | 1/2007 | EP | 1001928 | B1 | 4/2005 |
| CN | 1914154 | A | 2/2007 | EP | 1251737 | A1 | 4/2005 |
| CN | 1914155 | A | 2/2007 | EP | 1521736 | A1 | 4/2005 |
| CN | 1914156 | A | 2/2007 | EP | 1521738 | A2 | 4/2005 |
| CN | 1914157 | A | 2/2007 | EP | 1603865 | A1 | 12/2005 |
| CN | 1914158 | A | 2/2007 | EP | 1324976 | B1 | 2/2006 |
| CN | 1914159 | A | 2/2007 | EP | 134978 | B1 | 3/2006 |
| CN | 1914160 | A | 2/2007 | EP | 1214975 | B1 | 3/2006 |
| CN | 1914161 | A | 2/2007 | EP | 1648860 | A1 | 4/2006 |
| CN | 1914162 | A | 2/2007 | EP | 891323 | B1 | 6/2006 |
| CN | 1914165 | A | 2/2007 | EP | 1226147 | B1 | 6/2006 |
| CN | 1914166 | A | 2/2007 | EP | 1438317 | B1 | 6/2006 |
| CN | 1914167 | A | 2/2007 | EP | 1682561 | A1 | 7/2006 |
| CN | 1914216 | A | 2/2007 | EP | 1448668 | B1 | 8/2006 |
| CN | 1307237 | C | 3/2007 | EP | 1587621 | B1 | 8/2006 |
| CN | 1315790 | C | 5/2007 | EP | 1713759 | A1 | 10/2006 |
| CN | 1318432 | C | 5/2007 | EP | 1713761 | A1 | 10/2006 |
| CN | 1997624 | A | 7/2007 | EP | 1713762 | A1 | 10/2006 |
| CN | 1331843 | C | 8/2007 | EP | 1713766 | A1 | 10/2006 |
| CN | 101020641 | A | 8/2007 | EP | 1716102 | A2 | 11/2006 |
| CN | 101035799 | A | 9/2007 | EP | 1716103 | A1 | 11/2006 |
| CN | 101043946 | A | 9/2007 | EP | 1716104 | A1 | 11/2006 |
| CN | 100348322 | C | 11/2007 | EP | 1716105 | A1 | 11/2006 |
| CN | 100351227 | C | 11/2007 | EP | 1716106 | A1 | 11/2006 |
| CN | 100352824 | C | 12/2007 | EP | 1716107 | A1 | 11/2006 |
| CN | 100361966 | C | 1/2008 | EP | 1716109 | A1 | 11/2006 |
| CN | 100364666 | C | 1/2008 | EP | 1610893 | B1 | 3/2007 |
| CN | 1068307 | C | 7/2011 | EP | 1621531 | B1 | 3/2007 |
| DE | 1807088 | U | 3/1960 | EP | 1438132 | B1 | 4/2007 |
| DE | 1807088 | A1 | 6/1969 | EP | 1799697 | A1 | 6/2007 |
| DE | 2055747 | A1 | 5/1971 | EP | 1713764 | B1 | 8/2007 |
| DE | 1593277 | B2 | 8/1973 | EP | 1713816 | B1 | 8/2007 |
| DE | 1593277 | C3 | 3/1974 | EP | 1825914 | A1 | 8/2007 |
| DE | 2700904 | C2 | 10/1983 | EP | 1448620 | B1 | 6/2008 |
| DE | 68909466 | T2 | 3/1994 | EP | 1817108 | B1 | 6/2008 |
| DE | 10136488 | A1 | 2/2003 | EP | 1713760 | B1 | 7/2008 |
| DE | 10150285 | A1 | 4/2003 | EP | 1571172 | B1 | 10/2008 |
| DE | 10350999 | A1 | 6/2005 | EP | 1988998 | A1 | 11/2008 |
| DE | 102004004696 | A1 | 8/2005 | EP | 1265832 | B1 | 5/2009 |
| EP | 0001899 | B1 | 3/1982 | EP | 1592659 | B1 | 7/2009 |
| EP | 123438 | B1 | 7/1987 | EP | 1586598 | B1 | 9/2009 |
| EP | 160296 | B1 | 10/1988 | EP | 2098106 | A1 | 9/2009 |
| EP | 268448 | B1 | 9/1991 | EP | 1567478 | B1 | 10/2009 |
| EP | 510689 | A1 | 10/1992 | EP | 1682559 | B1 | 12/2009 |
| EP | 248643 | B1 | 3/1993 | EP | 1630166 | B1 | 2/2010 |
| EP | 336314 | B1 | 9/1993 | FR | 1544656 | A | 11/1968 |
| EP | 464691 | B1 | 12/1993 | FR | 2015115 | A5 | 4/1970 |

| | | | | | | |
|---|---|---|---|---|---|---|
| FR | 1603513 | A | 5/1971 | JP | 02818503 B2 | 10/1998 |
| FR | 2069411 | A5 | 9/1971 | JP | 10512879 A | 12/1998 |
| FR | 2845379 | B1 | 12/2004 | JP | 11501660 A | 2/1999 |
| FR | 2873696 | A1 | 2/2006 | JP | 11504262 A | 4/1999 |
| FR | 2873696 | B1 | 10/2006 | JP | 02911608 B2 | 6/1999 |
| GB | 0219474 | A | 7/1924 | JP | 11507297 A | 6/1999 |
| GB | 1104140 | A | 2/1968 | JP | 03001298 B2 | 1/2000 |
| GB | 1203702 | A | 9/1970 | JP | 03069915 B2 | 7/2000 |
| GB | 1213175 | A | 11/1970 | JP | 2001500135 A | 1/2001 |
| GB | 1429169 | A | 3/1976 | JP | 2001506250 A | 5/2001 |
| GB | 1429621 | A | 3/1976 | JP | 2001512097 A | 8/2001 |
| GB | 1436932 | A | 5/1976 | JP | 03205587 B2 | 9/2001 |
| GB | 1458322 | A | 12/1976 | JP | 2001516640 A | 10/2001 |
| GB | 1482909 | A | 8/1977 | JP | 03285878 B2 | 5/2002 |
| GB | 2007521 | A | 5/1979 | JP | 2002517473 A | 6/2002 |
| GB | 1565443 | A | 4/1980 | JP | 03320424 B2 | 9/2002 |
| GB | 1594694 | A | 8/1981 | JP | 2002533221 A | 10/2002 |
| GB | 2007521 | B | 6/1982 | JP | 03380543 B2 | 2/2003 |
| HK | 1025950 | A1 | 7/2003 | JP | 2003510385 A | 3/2003 |
| HK | 1026383 | A1 | 7/2004 | JP | 2003526688 A | 9/2003 |
| HK | 1052364 | A1 | 5/2007 | JP | 03478399 B2 | 12/2003 |
| JP | 48028423 | Y1 | 8/1973 | JP | 2004501058 A | 1/2004 |
| JP | 48028423 | B | 9/1973 | JP | 2004507550 A | 3/2004 |
| JP | 49043924 | Y1 | 12/1974 | JP | 03519410 B2 | 4/2004 |
| JP | 50059324 | U | 6/1975 | JP | 033535172 A | 6/2004 |
| JP | 50059326 | U | 6/1975 | JP | 03553952 B2 | 8/2004 |
| JP | 51007649 | B | 3/1976 | JP | 2004534032 A | 11/2004 |
| JP | 52012698 | B | 4/1977 | JP | 20004535929 A | 12/2004 |
| JP | 1013127 | C | 9/1980 | JP | 03621133 B2 | 2/2005 |
| JP | 55047031 | B | 11/1980 | JP | 2005503140 A | 2/2005 |
| JP | 57156454 | U | 10/1982 | JP | 2005505610 A | 2/2005 |
| JP | 57156455 | U | 10/1982 | JP | 2005505611 A | 2/2005 |
| JP | 57179144 | U | 11/1982 | JP | 2005510588 A | 4/2005 |
| JP | 1136333 | C | 2/1983 | JP | 2005510605 A | 4/2005 |
| JP | 58067658 | U | 5/1983 | JP | 2004509942 | 10/2005 |
| JP | 58126892 | U | 8/1983 | JP | 2005533095 A | 11/2005 |
| JP | 1170710 | C | 10/1983 | JP | 2005533096 A | 11/2005 |
| JP | 58159452 | U | 10/1983 | JP | 2005538075 A | 12/2005 |
| JP | 60044295 | A | 3/1985 | JP | 03739404 B2 | 1/2006 |
| JP | 60044295 | B | 10/1985 | JP | 2004534032 | 1/2006 |
| JP | 62294694 | A | 12/1987 | JP | 2004535929 | 1/2006 |
| JP | 63135363 | U | 9/1988 | JP | 2006000451 A | 1/2006 |
| JP | 1013127 | Y2 | 4/1989 | JP | 2006511591 A | 4/2006 |
| JP | 1209830 | A | 8/1989 | JP | 2006519797 A | 8/2006 |
| JP | 1136333 | U | 9/1989 | JP | 2006528616 A | 12/2006 |
| JP | 1050220 | B | 10/1989 | JP | 2007083057 A | 4/2007 |
| JP | 1173751 | U | 12/1989 | JP | 2007509885 A | 4/2007 |
| JP | 1565159 | C | 6/1990 | JP | 2007509886 A | 4/2007 |
| JP | 3001298 | B | 1/1991 | JP | 2007509887 A | 4/2007 |
| JP | 1615749 | C | 8/1991 | JP | 2007519516 A | 7/2007 |
| JP | 3205587 | A | 9/1991 | JP | 2007519663 A | 7/2007 |
| JP | 1627124 | C | 11/1991 | JP | 2007519664 A | 7/2007 |
| JP | 1627146 | C | 11/1991 | JP | 2007519666 A | 7/2007 |
| JP | 3069915 | B | 11/1991 | JP | 2007519667 A | 7/2007 |
| JP | 3285878 | A | 12/1991 | JP | 2007519670 A | 7/2007 |
| JP | 1642102 | C | 2/1992 | JP | 2007519671 A | 7/2007 |
| JP | 4012248 | Y2 | 3/1992 | JP | 2007519672 A | 7/2007 |
| JP | 4057050 | U | 5/1992 | JP | 2007519673 A | 7/2007 |
| JP | 4166155 | A | 6/1992 | JP | 2007519674 A | 7/2007 |
| JP | 4230254 | A | 8/1992 | JP | 2007519675 A | 7/2007 |
| JP | 4057050 | B | 9/1992 | JP | 2007519677 A | 7/2007 |
| JP | 4060532 | B | 9/1992 | JP | 2007522122 A | 8/2007 |
| JP | 4118676 | U | 10/1992 | JP | 04012248 B2 | 11/2007 |
| JP | 4128141 | U | 11/1992 | JP | 2006515323 | 2/2008 |
| JP | 1729140 | C | 1/1993 | JP | 04057050 B2 | 3/2008 |
| JP | 1811422 | C | 12/1993 | JP | 04060532 B2 | 3/2008 |
| JP | 7025841 | Y2 | 6/1995 | JP | 2006512918 | 5/2008 |
| JP | 7188144 | A | 7/1995 | JP | 2008515831 A | 5/2008 |
| JP | 2037346 | C | 3/1996 | JP | 2008516907 A | 5/2008 |
| JP | 8504814 | A | 5/1996 | JP | 04118676 B2 | 7/2008 |
| JP | 8157795 | A | 6/1996 | JP | 04128141 B2 | 7/2008 |
| JP | 2098106 | C | 10/1996 | JP | 04166155 B2 | 10/2008 |
| JP | 02521777 | Y2 | 1/1997 | JP | 04230254 B2 | 2/2009 |
| JP | 02623448 | B2 | 6/1997 | KR | 198802621 Y1 | 7/1988 |
| JP | 9505586 | A | 6/1997 | KR | 198802296 B | 10/1988 |
| JP | 9512013 | A | 12/1997 | KR | 198802296 B1 | 10/1988 |
| JP | 10505101 | A | 5/1998 | KR | 1999003458 B1 | 5/1990 |
| JP | 10506911 | A | 7/1998 | KR | 199008166 B1 | 11/1990 |
| JP | 10509954 | A | 9/1998 | KR | 199104132 B1 | 6/1991 |

| | | | | | | | |
|---|---|---|---|---|---|---|---|
| KR | 199205087 Y1 | 7/1992 | | WO | WO02092551 A2 | 11/2002 |
| KR | 2006132885 A | 12/2006 | | WO | WO03011457 A1 | 2/2003 |
| MX | 2004PA002764 A | 6/2004 | | WO | WO03018540 A1 | 3/2003 |
| NL | 197700262 A | 7/1977 | | WO | WO03024919 A1 | 3/2003 |
| NL | 188158 C | 4/1992 | | WO | WO03031392 A1 | 4/2003 |
| SU | 677650 A | 7/1979 | | WO | WO03033141 A1 | 4/2003 |
| TW | 387874 B | 4/2000 | | WO | WO03033509 A1 | 4/2003 |
| TW | 400249 B | 8/2000 | | WO | WO03046019 A1 | 6/2003 |
| TW | 453983 B | 9/2001 | | WO | WO03046049 A1 | 6/2003 |
| TW | 455576 B | 9/2001 | | WO | WO03068729 A1 | 8/2003 |
| TW | 457244 B | 10/2001 | | WO | WO03076394 A1 | 9/2003 |
| TW | 458959 B | 10/2001 | | WO | WO2004007431 A1 | 1/2004 |
| TW | 519496 B | 2/2003 | | WO | WO2004007432 A1 | 1/2004 |
| TW | 527340 B | 4/2003 | | WO | WO2004007435 A2 | 1/2004 |
| TW | 576837 B | 2/2004 | | WO | WO2004007508 A2 | 1/2004 |
| TW | 580489 B | 3/2004 | | WO | WO0168247 C1 | 6/2004 |
| TW | 580490 B | 3/2004 | | WO | WO2004060855 A1 | 7/2004 |
| TW | 584623 B | 4/2004 | | WO | WO2004064994 A2 | 8/2004 |
| TW | 592821 B | 6/2004 | | WO | WO2004065352 A2 | 8/2004 |
| TW | 226345 B | 1/2005 | | WO | WO2004080924 A2 | 9/2004 |
| TW | 233438 B | 6/2005 | | WO | WO2004080948 A1 | 9/2004 |
| TW | 245780 B | 12/2005 | | WO | WO2004087314 A1 | 10/2004 |
| TW | 266650 B | 11/2006 | | WO | WO2005019160 A1 | 3/2005 |
| TW | 453985 B | 9/2010 | | WO | WO2005042156 A1 | 5/2005 |
| WO | WO7900193 A1 | 4/1979 | | WO | WO2005042157 A1 | 5/2005 |
| WO | WO9414752 A1 | 7/1994 | | WO | WO2005042547 A1 | 5/2005 |
| WO | WO9514659 A1 | 6/1995 | | WO | WO2005042549 A1 | 5/2005 |
| WO | WO9528228 A1 | 10/1995 | | WO | WO2005073167 A1 | 8/2005 |
| WO | WO9529153 A1 | 11/1995 | | WO | WO2005073168 A1 | 8/2005 |
| WO | WO9611182 A1 | 4/1996 | | WO | WO2005073169 A1 | 8/2005 |
| WO | WO9616022 A1 | 5/1996 | | WO | WO2005073170 A1 | 8/2005 |
| WO | WO9622968 A1 | 8/1996 | | WO | WO2005073171 A1 | 8/2005 |
| WO | WO9629303 A1 | 9/1996 | | WO | WO2005073172 A1 | 8/2005 |
| WO | WO9703040 A1 | 1/1997 | | WO | WO2005073173 A1 | 8/2005 |
| WO | WO9712857 A1 | 4/1997 | | WO | WO2005073174 A1 | 8/2005 |
| WO | WO9724183 A1 | 7/1997 | | WO | WO2005073175 A1 | 8/2005 |
| WO | WO9736855 A2 | 10/1997 | | WO | WO2005073176 A1 | 8/2005 |
| WO | WO9811051 A1 | 3/1998 | | WO | WO2005073178 A2 | 8/2005 |
| WO | WO98027054 A1 | 6/1998 | | WO | WO2005073179 A1 | 8/2005 |
| WO | WO9906146 A2 | 2/1999 | | WO | WO2005073241 A1 | 8/2005 |
| WO | WO9906356 | 2/1999 | | WO | WO2006040023 A1 | 4/2006 |
| WO | WO9906359 A1 | 2/1999 | | WO | WO2006042675 A2 | 4/2006 |
| WO | WO9913983 A1 | 3/1999 | | WO | WO2005073166 A3 | 3/2007 |
| WO | WO9964155 A1 | 12/1999 | | WO | WO2007051374 A1 | 5/2007 |
| WO | WO0001485 A2 | 1/2000 | | WO | WO2007096274 A1 | 8/2007 |
| WO | WO0037431 A1 | 6/2000 | | WO | 2007115936 | 10/2007 |
| WO | WO0121684 A1 | 3/2001 | | WO | WO2007115936 A2 | 10/2007 |
| WO | WO0136429 A1 | 5/2001 | | WO | WO2008008926 A2 | 1/2008 |
| WO | WO0168247 A2 | 9/2001 | | WO | WO2008008928 A2 | 1/2008 |
| WO | WO0211108 A1 | 2/2002 | | WO | WO2008008929 A2 | 1/2008 |
| WO | WO0213964 A2 | 2/2002 | | WO | WO2008008930 A2 | 1/2008 |
| WO | WO0218392 A1 | 3/2002 | | WO | WO2008028843 A1 | 3/2008 |
| WO | WO0226698 A1 | 4/2002 | | WO | WO2008062058 A1 | 5/2008 |
| WO | WO0230854 A2 | 4/2002 | | | | |
| WO | WO02053527 A1 | 7/2002 | | | | |

* cited by examiner

PROCESS FOR MAKING 2-SECONDARY-ALKYL-4,5-DI-(NORMAL-ALKYL)PHENOLS

CROSS-REFERENCE TO RELATED APPLICATIONS

This application claims benefit of priority from Provisional Application No. 61/105,185 filed Oct. 14, 2008. This application hereby incorporates by reference Provisional Application No. 61/105,185 in its entirety.

FIELD OF THE INVENTION

The invention relates to the preparation of alkylated phenols. More specifically, the invention relates to a process for the manufacture of 2-secondary-alkyl-4,5-di-(normal-alkyl) phenols.

BACKGROUND OF THE INVENTION

There are many important commercial applications of organophosphorus compounds derived from aromatic alcohols which include their use as antioxidants, stabilizers, antiwear additives, and as ligands for various catalytic processes, for example olefin hydrocyanation or hydroformylation. An ingredient for making some monodentate or bidentate organophosphorus compounds includes 2,2'-biphenol compounds with the general Structure I. These 2,2'-biphenols are generally made by oxidative coupling of the corresponding phenols of Structure II, for example as disclosed in the published U.S. Patent Application 2003/0100802.

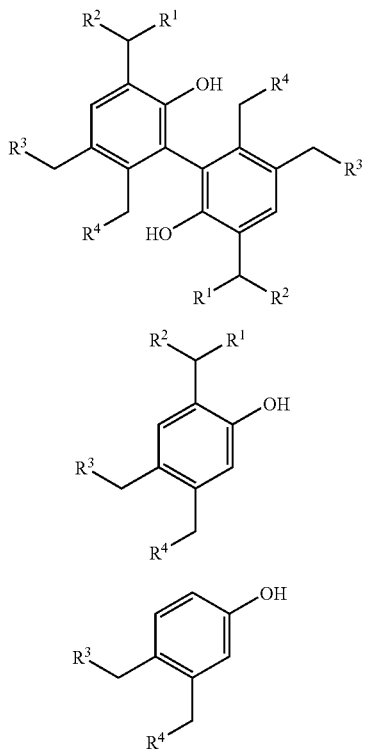

One method for manufacturing 2-secondary-alkyl-4,5-di-(normal-alkyl)phenols of general Structure II is the alkylation of corresponding 3,4-di-(normal-alkyl)phenols of general Structure III. Houben-Weyl, Vol. 6/1C pages (955-985), G. Thieme Verlag, Stuttgart 1976, teaches general methods for the alkylation of phenols with alkenes using homogeneous and heterogeneous acid catalysts. With regard to the latter catalysts, U.S. Pat. No. 3,037,052, for example, discloses the use of macroreticular ion exchange resins containing sulfonic acid groups as catalysts for the alkylation of phenols with alkenes. This reference states that "macroreticular" refers to a unique porous structure that is developed when monoethylenically unsaturated monomers are copolymerized with polyvinylidene monomers in the presence of certain compounds.

J. Kamis [Collection of Czechoslovak Chemical Communications 1964, 29(12), 3176-8] reports the alkylation of 3,4-dimethylphenol with the reactive 1,1-disubstituted alkene, isobutylene, in the presence of a cation exchange resin Allassion CS. However, both catalyst activity and selectivity to 2-tertiary-butyl-4,5-dimethylphenol are reported to be low. S. P. Starkov and L. V. Glushkova (Journal of Applied Chemistry of the USSR 1967, 40, pages 209 and 1583) describe the alkylation of 3,4-dimethylphenol with the reactive 1,2-disubstituted alkenes, 2-hexene and cyclohexene, in the presence of the cation exchange resin KU-2. Poor catalyst activity requires high loadings (50%) and 3,4-dimethylphenol conversion is maintained below 50% to achieve acceptable chemical yields to the desired 2-alkyl-4,5-dimethylphenol. High catalyst loadings, low 3,4-dimethylphenol conversion, and low selectivity to the desired 2-alkyl-4,5-di-(normal-alkyl)phenol severely limit reactor productivity and add to the manufacturing cost.

U.S. Pat. No. 4,236,031 discloses a process for preparing 5-t-butyl alkylphenols comprising reacting a 3-alkylphenol or a 2,3-dialkylphenol with isobutylene in the presence of an effective amount of a sulfonated polystyrene catalyst crosslinked with divinylbenzene at a temperature of at least 100° C. U.S. Pat. No. 4,236,031 also discloses a process for preparing 6-t-butyl alkylphenols comprising reacting a 3-alkylphenol or a 2,3-dialkylphenol with isobutylene in the presence of an effective amount of a sulfonated polystyrene catalyst crosslinked with divinylbenzene at a temperature in the range of 50° C. to 90° C. U.S. Pat. No. 4,380,677 discloses the selective dialkylation of 4-alkylphenols with isobutylene using an alkylation catalyst which is a macroreticular cation exchange resin bearing sulfonic acid groups with an internal surface area greater than about 200 square meter per gram ($m^2/g$) and an average pore diameter less than 120 Angstroms (Å).

The use of macroreticular cation exchange resins containing sulfonic acid groups as catalysts for the alkylation of substituted phenols with alkenes has been disclosed. However, the selection and usage of such a catalyst for the selective monoalkylation of 3,4-di-(normal-alkyl)phenols with alkenes to produce 2-secondary-alkyl-4,5-di-(normal-alkyl) phenols and the preferred properties of such a catalyst to reach high productivity in this reaction have not been previously reported. An improved synthesis of 2-secondary-alkyl-4,5-di-(normal-alkyl)phenols is desired. In particular, a process for making the desirable 2-iso-propyl-4,5-dimethylphenol from 3,4-dimethylphenol and propylene that is characterized by the combination of (1) high reaction productivity at low catalyst to reactant ratios, (2) high propylene and 3,4-dimethylphenol conversions, and (3) good selectivity to the 2-iso-propyl-4,5-dimethylphenol isomer is desired. The present invention describes such a process, as well as the associated benefits derived from the separation of 2-iso-propyl-4,5-dimethylphenol from co-products.

SUMMARY OF THE INVENTION

In a first aspect, the present invention provides a process for making 2-secondary-alkyl-4,5-di-(normal-alkyl)phenols of Structure II, said process comprising contacting a 3,4-di-(normal-alkyl)phenol of Structure III with an alkene in the presence of a heterogeneous acid catalyst and optionally in the presence of a solvent at a first temperature in the range of about 70° C. to about 170° C. to produce a first reaction mixture comprising 2-secondary-alkyl-4,5-di-(normal-alkyl)phenol;

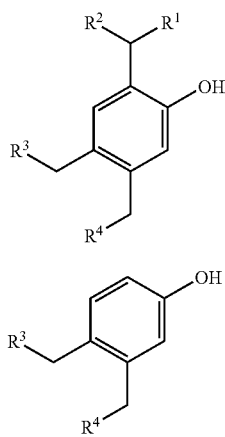

wherein, in Structures II and III:
  $R^1$ is selected from the group consisting of unsubstituted phenyl; phenyl substituted with one or more linear or branched $C_1$ to $C_6$ alkyl groups; and linear or branched $C_1$ to $C_9$ alkyl groups;
  $R^2$ is selected from the group consisting of linear or branched $C_1$ to $C_{14}$ alkyl groups;
  $R^3$ and $R^4$ are independently selected from the group consisting of hydrogen and linear or branched $C_1$ to $C_{16}$ alkyl groups;
wherein, the alkene contains 3 to 16 carbon atoms; and
wherein the heterogeneous acid catalyst is a macroreticular cation exchange resin containing sulfonic acid groups and having an acid capacity of at least 4 equivalents acid per kilogram.

Another aspect of the invention is the process further comprising heating the first reaction mixture at a second temperature in the range of about 120° C. to about 175° C. to produce a second reaction mixture comprising predominantly 2-secondary-alkyl-4,5-di-(normal-alkyl)phenol, wherein the second temperature is greater than or equal to the first temperature.

Another aspect of the invention is the process wherein the solvent comprises at least one saturated aliphatic hydrocarbon.

Another aspect of the invention is the process further comprising separating at least a portion of the catalyst from the second reaction mixture to produce a third reaction mixture depleted in catalyst and comprising 2-secondary-alkyl-4,5-di-(normal-alkyl)phenol.

Another aspect of the invention is the process further comprising separating at least a portion of the 2-secondary-alkyl-4,5-di-(normal-alkyl)phenol from the third reaction mixture.

Another aspect of the invention is the process further comprising separating at least a portion of the 2-secondary-alkyl-4,5-di-(normal-alkyl)phenol from the third reaction mixture and returning at least some of the remaining portion of the third reaction mixture depleted of 2-secondary-alkyl-4,5-di-(normal-alkyl)phenol to one or both of the steps of contacting a 3,4-di-(normal-alkyl)phenol with an alkene, or heating the first reaction mixture at a second, temperature in the range of about 120° C. to about 175° C. to produce a second reaction mixture comprising predominantly 2-secondary-alkyl-4,5-di-(normal-alkyl)phenol, wherein the second temperature is greater than or equal to the first temperature.

Another aspect of the invention is the process further comprising separating at least a portion of any 3,4-di-(normal-alkyl)phenol of Structure III from the third reaction mixture and returning at least a portion of the 3,4-di-(normal-alkyl)phenol to the step of contacting the 3,4-di-(normal-alkyl)phenol with an alkene.

Another aspect of the invention is the process wherein the third reaction mixture further comprises at least one di-(secondary-alkyl)phenol selected from the group consisting of compounds of Structure VI, Structure VII, and a mixture thereof, wherein at least a portion of the di-(secondary-alkyl)phenol is separated from the third reaction mixture,

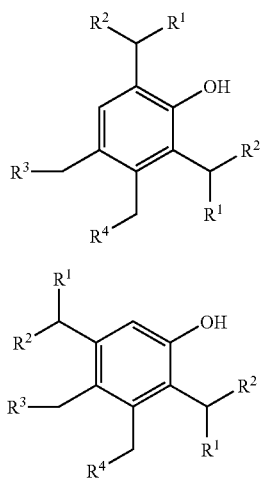

and wherein, in Structure VI and Structure VII, $R^1$ is selected from the group consisting of unsubstituted phenyl; phenyl substituted with one or more linear or branched $C_1$ to $C_6$ alkyl groups; and linear or branched $C_1$ to $C_9$ alkyl groups; $R^2$ is selected from the group consisting of linear or branched $C_1$ to $C_{14}$ alkyl groups; and $R^3$ and $R^4$ are independently selected from the group consisting of hydrogen and linear or branched $C_1$ to $C_{16}$ alkyl groups.

Another aspect of the invention is the process wherein at least a portion of the di-(secondary-alkyl)phenol which is separated from the third reaction mixture is returned to the step of contacting the 3,4-di-(normal-alkyl)phenol with an alkene or to the step of heating the first reaction mixture at a second temperature.

Another aspect of the invention is the process wherein at least a portion of the di-(secondary-alkylphenol which is separated from the third reaction mixture is returned to the step of heating the first reaction mixture at a second temperature to produce a second reaction mixture.

Another aspect of the invention is the process wherein at least a portion of the di-(secondary-alkyl)phenol which is separated from the third reaction mixture is purged from the process.

Another aspect of the invention is the process wherein the third reaction mixture further comprises at least one mono-(secondary-alkyl)phenol selected from the group consisting of Structure IV, Structure V, and a mixture thereof, wherein at least a portion of the mono-(secondary-alkyl)phenol is separated from the third reaction mixture and at least a portion is returned to the step of contacting a 3,4-di-(normal-alkyl)phenol with an alkene or to the step of heating the first reaction mixture at a second temperature,

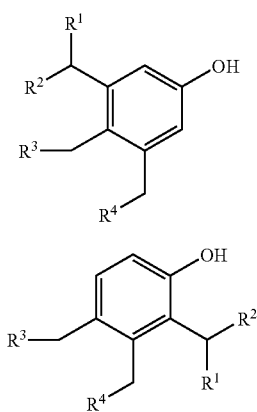

and wherein, in Structure IV and Structure V, $R^1$ is selected from the group consisting of unsubstituted phenyl; phenyl substituted with one or more linear or branched $C_1$ to $C_6$ alkyl groups; and linear or branched $C_1$ to $C_9$ alkyl groups; $R^2$ is selected from the group consisting of linear or branched $C_1$ to $C_{14}$ alkyl groups; and $R^3$ and $R^4$ are independently selected from the group consisting of hydrogen and linear or branched $C_1$ to $C_{16}$ alkyl groups.

Another aspect of the invention is the process wherein the separation is by distillation.

Another aspect of the invention is the process wherein the distillation provides at least one distillate fraction and a distillation tails, and wherein the process further comprises returning at least a portion of at least one distillate fraction to the step of contacting a 3,4-di-(normal-alkyl)phenol with an alkene.

Another aspect of the invention is the process wherein the distillation is continuous.

Another aspect of the invention is the process wherein the distillation is batch.

Another aspect of the invention is the process wherein the separation is by crystallization.

Another aspect of the invention is the process wherein at least a portion of the mother liquor obtained from the crystallization is returned to the step of contacting a 3,4-di-(normal-alkyl)phenol with an alkene or to the step of heating the first reaction mixture at a second temperature.

Another aspect of the invention is the process wherein the crystallization is continuous.

Another aspect of the invention is the process wherein the crystallization is batch.

Another aspect of the invention is the process wherein the first reaction mixture and the second reaction mixture are produced in a batch or semi-batch manner in the same reaction vessel.

Another aspect of the invention is the process wherein the first reaction mixture and the second reaction mixture are produced in a continuous manner in separate reaction vessels.

Another aspect of the invention is the process wherein $R^1$ is a methyl, $R^2$ is a methyl or ethyl, $R^3$ is a hydrogen, methyl or ethyl and $R^4$ is a hydrogen, methyl or ethyl.

Another aspect of the invention is the process wherein the alkylene is propylene.

Another aspect of the invention is the process wherein the 3,4-di-(normal-alkyl)phenol is 3,4-dimethylphenol and the alkene is propylene.

Another aspect of the invention is the process wherein the molar ratio of alkene to 3,4-di-(normal-alkyl)phenol is in the range of 0.90:1.0 to 1.25:1.0.

Another aspect of the invention is the process wherein the macroreticular cation exchange resin has a surface area greater than about 40 m²/g.

Another aspect of the invention is the process wherein at least about 70% of the surface area of the macroreticular cation exchange resin is in pores having a pore diameter from 0.009 μm to 0.027 μm as measured by mercury intrusion porosimetry.

Another aspect of the invention is a process to improve yield in the synthesis of 2-secondary-alkyl-4,5-di-(normal-alkyl)phenols of Structure II, the process comprising:

heating to a temperature in the range of about 120° C. to about 175° C. in the presence of a heterogeneous acid catalyst a first reaction mixture comprising 2-secondary-alkyl-4,5-di-(normal-alkyl)phenol and at least one compound selected from the group consisting of compounds of Structure IV, V, VI, VII, and a mixture thereof, the first reaction mixture being obtained by alkylation of a 3,4-di-(normal-alkyl)phenol with an alkene in the presence of the heterogeneous acid catalyst, to obtain a second reaction mixture comprising 2-secondary-alkyl-4,5-di-(normal-alkyl)phenol;

wherein the yield of the 2-secondary-alkyl-4,5-di-(normal-alkyl)phenol is increased after heating the second reaction mixture;

wherein, in Structure II, IV, V, VI, and VII:

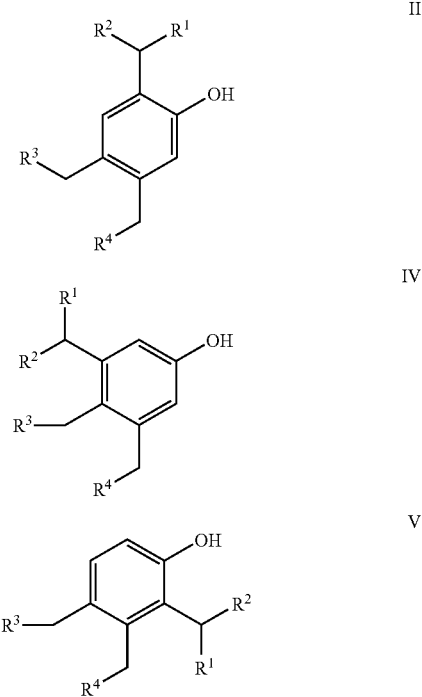

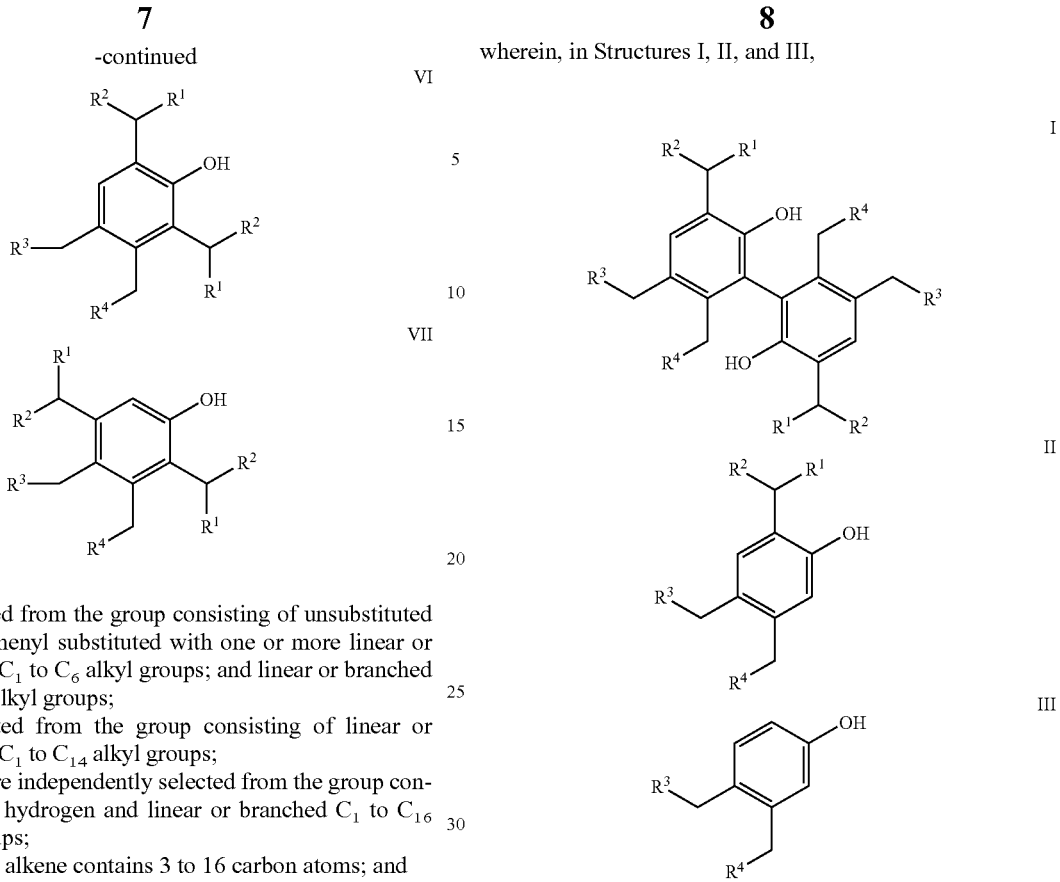

-continued

VI

VII

R¹ is selected from the group consisting of unsubstituted phenyl; phenyl substituted with one or more linear or branched $C_1$ to $C_6$ alkyl groups; and linear or branched $C_1$ to $C_9$ alkyl groups;

R² is selected from the group consisting of linear or branched $C_1$ to $C_{14}$ alkyl groups;

R³ and R⁴ are independently selected from the group consisting of hydrogen and linear or branched $C_1$ to $C_{16}$ alkyl groups;

wherein, the alkene contains 3 to 16 carbon atoms; and wherein the heterogeneous acid catalyst is a strongly acidic macroreticular cation exchange resin containing sulfonic acid groups and having an acid capacity of at least 4 equivalents acid per kilogram.

Another aspect of the invention is the process wherein the 3,4-di-(normal-alkyl)phenol is 3,4-dimethylphenol and the alkene is propylene.

Another aspect of the invention is the process wherein the macroreticular cation exchange resin has a surface area greater than about 40 m²/g.

Another aspect of the invention is the process wherein at least about 70% of the surface area of the macroreticular cation exchange resin is in pores with a pore diameter from 0.009 μm to 0.027 μm as measured by mercury intrusion porosimetry.

Another aspect of the invention is a process for making a compound of Structure I, the process comprising:

(a) contacting a 3,4-di-(normal-alkyl)phenol of Structure III with an alkene in the presence of a heterogeneous acid catalyst and optionally in the presence of a solvent at a first temperature in the range of about 70° C. to about 170° C. to produce a first reaction mixture comprising a 2-secondary-alkyl-4,5-di-(normal-alkyl)phenol of Structure II;

(b) heating the first reaction mixture at a second temperature in the range of about 120° C. to about 175° C. in the presence of the heterogeneous acid catalyst, and optionally in the presence of a solvent, to produce a second reaction mixture comprising predominantly the 2-secondary-alkyl-4,5-di-(normal-alkyl)phenol of Structure II, wherein the second temperature is greater than or equal to the first temperature; and (c) performing oxidative coupling of the 2-secondary-alkyl-4,5-di-(normal-alkyl)phenol of Structure II to produce a compound of Structure I;

wherein, in Structures I, II, and III,

R¹ is selected from the group consisting of unsubstituted phenyl; phenyl substituted with one or more linear or branched $C_1$ to $C_6$ alkyl groups; and linear or branched $C_1$ to $C_9$ alkyl groups;

R² is selected from the group consisting of linear or branched $C_1$ to $C_{14}$ alkyl groups;

R³ and R⁴ are independently selected from the group consisting of hydrogen and linear or branched $C_1$ to $C_{16}$ alkyl groups;

wherein, the alkene contains 3 to 16 carbon atoms; and wherein the heterogeneous acid catalyst is a strongly acidic macroreticular cation exchange resin containing sulfonic acid groups and having an acid capacity of at least 4 equivalents acid per kilogram.

Another aspect of the invention is the process wherein the 3,4-di-(normal-alkyl)phenol is 3,4-dimethylphenol and the alkene is propylene.

Another aspect of the invention is the process wherein at least a portion of the 2-secondary-alkyl-4,5-di-(normal-alkyl)phenol of Structure II is isolated from the second reaction mixture prior to performing the oxidative coupling of step (c).

Another aspect of the invention is the process wherein the macroreticular cation exchange resin has a surface area greater than about 40 m²/g.

Another aspect of the invention is the process wherein at least about 70% of the surface area of the macroreticular cation exchange resin is in pores with a pore diameter from 0.009 μm to 0.027 μm as measured by mercury intrusion porosimetry.

DETAILED DESCRIPTION OF THE FIGURES

FIG. 1 graphically illustrates pore size distribution in the range of D=0.01 μm to 0.06 μm shown as incremental mercury intrusion volume δV in cm³/g versus the mean diameter <D> in μm of the pore for selected heterogeneous acid catalysts.

Figure 2:
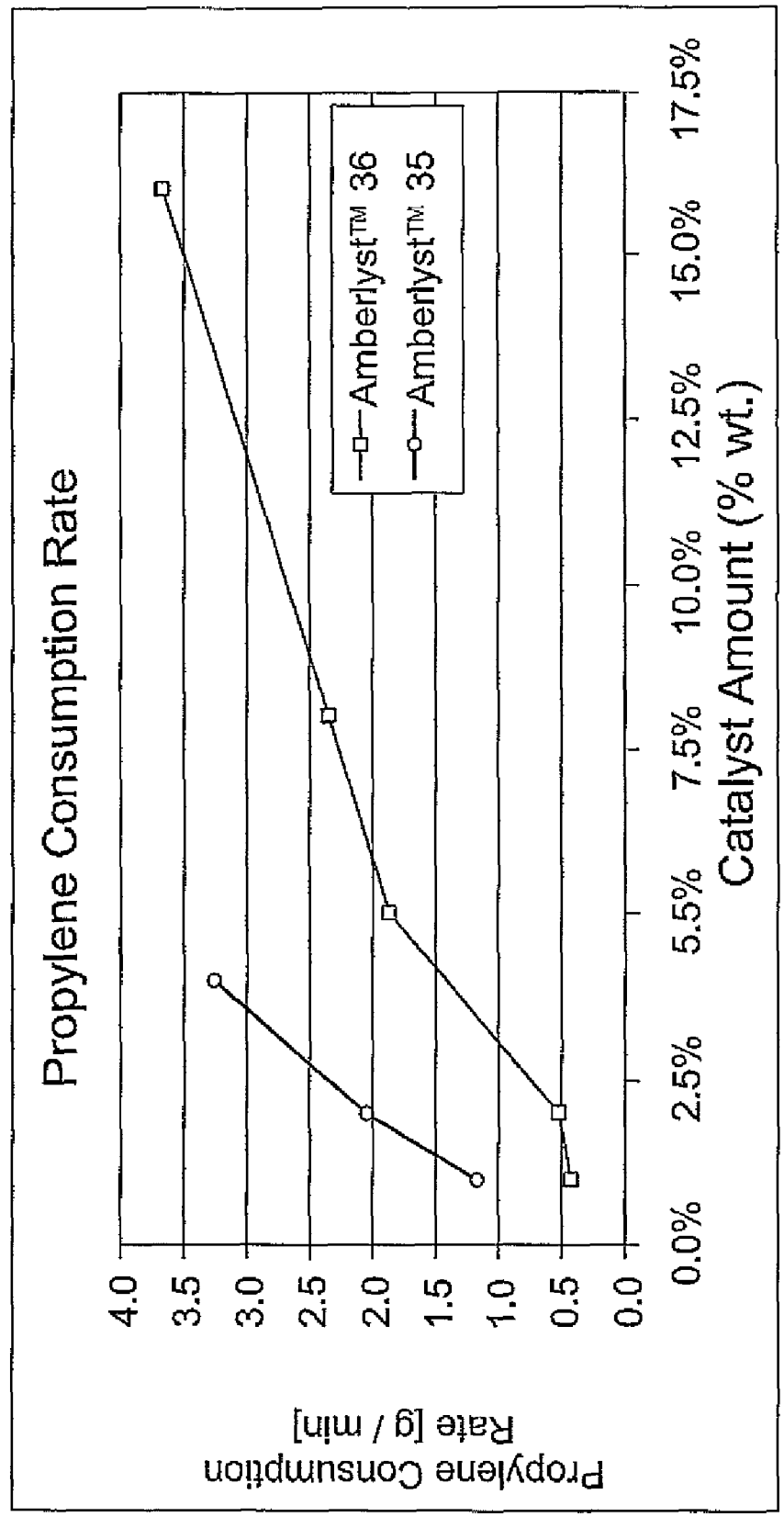

FIG. 2 graphically illustrates the propylene consumption rate for the alkylation of 3,4-dimethylphenol with propylene under identical conditions using different amounts of Amberlyst™ 35 and Amberlyst™ 36 catalysts.

Figure 3:
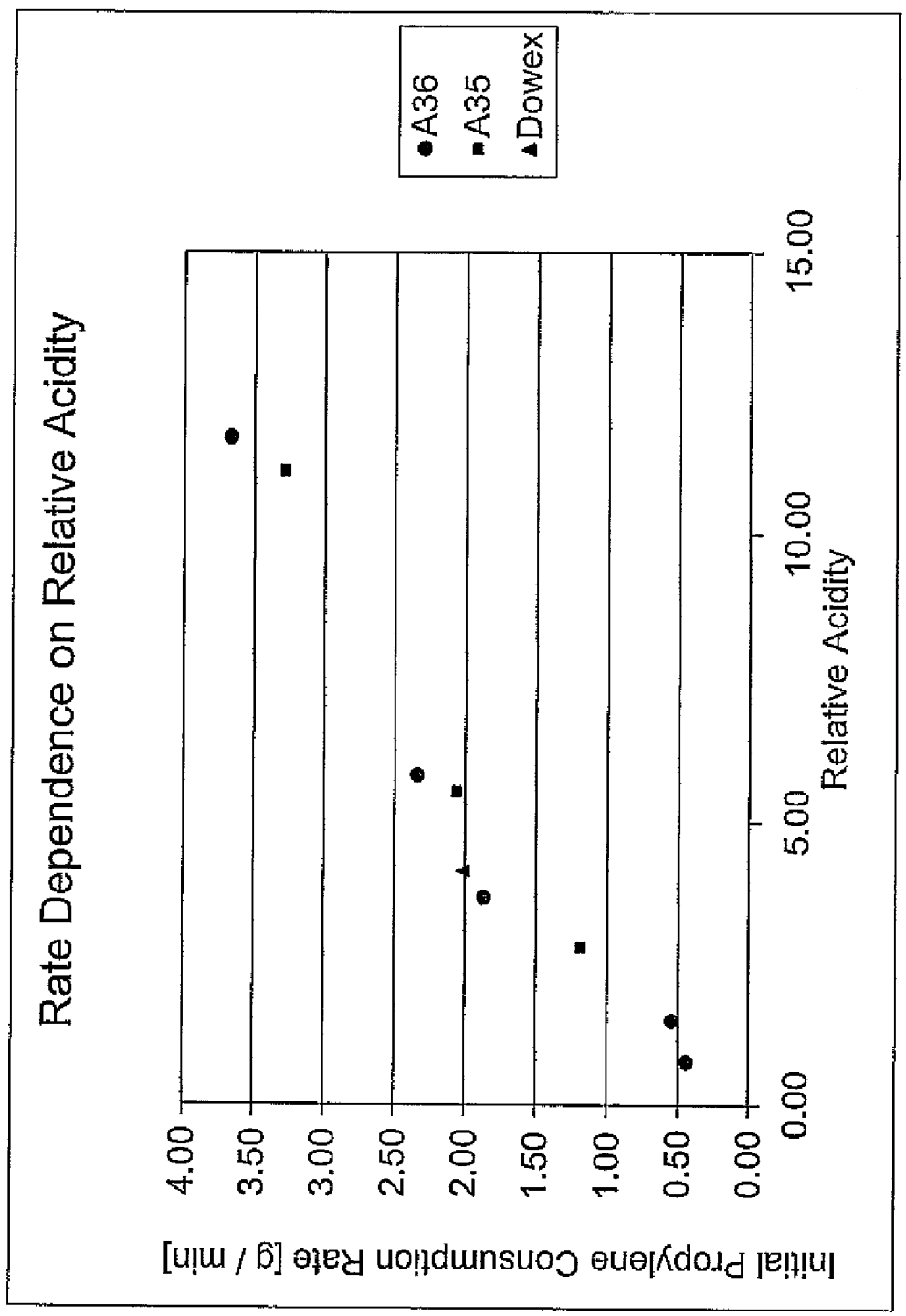

FIG. 3 graphically illustrates the relative acidity and propylene consumption rate during the propylation of 3,4-dimethylphenol with Amberlyst™ 35 ("A35"), Amberlyst™ 36 ("A36"), and Dowex™ DR-2030 ("Dowex") catalysts.

DETAILED DESCRIPTION OF THE INVENTION

High reaction productivity for the alkylation of 3,4-di-(normal-alkyl)phenols of Structure III with alkenes at moderate temperatures to give 2-secondary-alkyl-4,5-di-(normal-alkyl)phenols of the general Structure II can be achieved when a macroreticular cation exchange resin containing sulfonic acid groups and having an acid capacity of at least 4 equivalents acid per kilogram is used as a catalyst. The macroreticular cation exchange resin has a surface area greater than about 40 m²/g. At least about 70% of the surface area of the macroreticular cation exchange resin is in pores having a pore diameter from 0.009 μm to 0.027 μm, as measured by mercury intrusion porosimetry.

In order to prepare a 2-secondary-alkyl-4,5-di-(normal-alkyl)phenol selected from a member of the group represented by Structure II, a 3,4-di-(normal-alkyl)phenol selected from a member of the group represented by Structure III is contacted with an alkene in the presence of a heterogeneous acid catalyst at a temperature range of about 70° C. to about 170° C. to produce a reaction product mixture comprising the 2-secondary-alkyl-4,5-di-(normal-alkyl)phenol, the heterogeneous acid catalyst, optionally a solvent, and optionally alkene and 3,4-di-(normal-alkyl)phenol reactants.

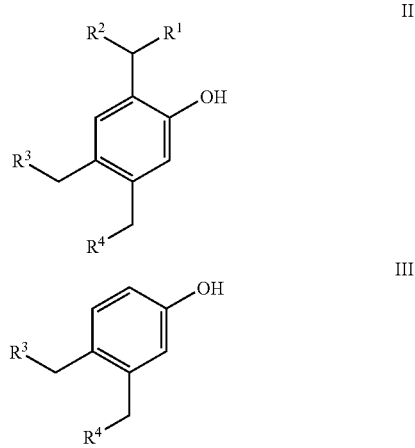

In Structures II and III, $R^1$ is selected from the group consisting of unsubstituted phenyl; phenyl substituted with one or more linear or branched $C_1$ to $C_6$ alkyl groups; and linear or branched $C_1$ to $C_9$ alkyl groups; $R^2$ is selected from the group consisting of linear or branched $C_1$ to $C_{14}$ alkyl groups; and $R^3$ and $R^4$ are independently selected from the group consisting of hydrogen and linear or branched $C_1$ to $C_{16}$ alkyl groups.

The heterogeneous acid catalyst comprises a strongly acidic macroreticular cation exchange resin containing sulfonic acid groups with a sufficient acid capacity, for example an acid capacity of at least 4 equivalents of acid per kilogram of catalyst. The macroreticular cation exchange resin has sufficient area, as well as sufficient distribution of that surface area in pores of appropriate diameter. For example, the macroreticular cation exchange resin has a surface area greater than about 40 m²/g, and at least about 70% of the surface area is in pores having a pore diameter from 0.009 μm to 0.027 μm (pore size range M in the Examples) as measured by mercury intrusion porosimetry. The catalyst is also thermally stable at the process temperatures employed, for example above about 120° C., as evidenced, by its continued activity upon recycle at reaction conditions. Examples of suitable catalysts are Amberlyst™ 35 and Amberlyst™ 36 sold by the Rohm and as Company.

The amount of catalyst used affects the reaction rate and depends on the particular process parameters, process step, and the reactants chosen. Process parameters to be considered are temperature, pressure, and reactant concentrations. For a batch process, catalyst loadings of about 1 percent by weight to about 100 percent by weight of the phenol reactant are generally suitable. For practical considerations in a batch process, catalyst loadings from about 1 percent by weight to about 30 percent by weight are suitable. However, in many cases a 2 percent by weight catalyst loading allows for complete conversion of the olefin within less than 3 hours of reaction time, provided that the reaction parameters described below are maintained within the recommended ranges. An advantage of the process of the invention is the high productivity observed in a batch and semibatch process using a relatively small amount of catalyst. In a batch and semibatch process, the catalyst can be reused multiple times without significant loss of activity provided the operating temperature is maintained at or below the maximum recommended operating temperature of the catalyst. With these macroreticular cation exchange resins, high productivity at low catalyst loadings is also anticipated in a continuous reaction mode comprising a stationary catalyst in at least one stirred tank or fixed bed reactor. In such a continuous process, reaction fluid flow rates over a stationary catalyst of about 1 to about 5 m³ liquid per m³ catalyst per hour are suitable.

For the catalyst to be most effective, it must contain less than about 3 wt % water. Pre-conditioning of the catalyst prior to use is recommended, and methods for pre-conditioning catalyst are known in the art. Pre-conditioning of the catalyst can be achieved, for example, by heating the catalyst under vacuum or in an inert gas stream at temperatures above 100° C., but not above the recommended maximum operating temperature of the catalyst, for a period of about 2 to 24 hours. Inert gases may include, but not limited to, at least one selected from the group comprising nitrogen, argon, helium, carbon dioxide, and natural gas, Other non-exclusive methods of pre-conditioning catalyst include, for example, distillation of a portion of the 3,4-di-(normal-alkyl)phenol reactant from the catalyst, azeotropic distillation of a solvent-water mixture from the catalyst, and passing a pre-determined amount of the dry 3,4-di-(normal-alkyl)phenol reactant or a dry solvent at a pre-determined temperature through a packed column of the catalyst. Pre-conditioning methods may be used singly or in combination with one another. It is also important to keep the level of water in the 3,4-di-(normal-alkyl)phenol and in the alkene at a sufficiently low level that the catalyst contains less than 3 wt % water in the reaction mixture. If necessary, the 3,4-di-(normal-alkyl)phenol, the alkene, or both may be dried before use.

The alkene may contain 3 to 16 carbon atoms. Useful alkenes include, for example, propylene, 1-butene, 2-butene, 2-pentene, styrene, and allylbenzene. The alkene may be introduced into the reaction vessel as a liquid or a gas. The alkene may be added continuously or in portions and consumed instantly provided that the catalyst loading and reaction temperature are sufficiently high. The quantity of alkene added to achieve a 95% or higher conversion of the 3,4-di-(normal-alkyl)phenol reactant of Structure III to the corresponding 2-secondary-alkyl-3,4-di-(normal-alkyl)phenol of Structure II product should be in the range of 0.9:1.0 to 1.25:1.0 molar equivalents of alkene per mole of 3,4-di-(normal-alkyl)phenol reactant.

The reaction can be performed in the absence of a solvent, in a predominately neat phenol reactant and product mixture, or optionally in the presence of a nonreactive solvent or solvent mixture, for example a saturated aliphatic hydrocarbon or a mixture of saturated aliphatic hydrocarbons. To maximize productivity, conversion, and selectivity to the desired product, the alkylation reaction of the present invention should be performed in reactor systems providing efficient contact between catalyst and reactants comprising the alkene and 3,4-di-(normal-alkyl)phenol. Such reactor systems are known in the art. For gaseous alkenes, sufficient mixing within the reactor between any vapor phase comprising the alkene and the liquid phase comprising the catalyst and 3,4-di-(normal-alkyl)phenol is important to achieve the highest productivity during the alkylation reaction.

Addition of catalyst and reactants to the reaction vessel and operation of said reaction vessel may take various forms to achieve the benefits of the invention. In one embodiment, after the 3,4-di-(normal-alkyl)phenol reactant, catalyst, and optionally a nonreactive solvent or solvent mixture are added to the reaction vessel, the temperature is raised to the desired temperature and the alkene is added all at once (in batch operation), in portions (in semi-batch operation), continuously (in semi-batch operation), or combinations thereof such that the reaction temperature stays within the predetermined temperature range. Alternatively, for continuous operation, the catalyst can be charged to the reaction vessel and the 3,4-di-(normal-alkyl)phenol, the optional solvent or solvent mixture, and the alkene can be added continuously, as separate or combined feeds.

Temperature ranges suitable for the process of this invention range from about 70° C. to about 170° C. and depend on the alkene and 3,4-di-(normal-alkyl)phenol reactants, the thermal stability of the catalyst, and the desired reaction productivity. For phenol propylation reactions, temperatures of about 120° C. to about 155° C., for example about 140° C. to about 155° C., are suitable. The pressure of a volatile alkene can have a significant impact on the reaction rate. Generally, higher pressures provide for a higher reaction rate. In most cases, an alkene partial pressure of 1 psig to 100 psig (108 kPa to 790 kPa) is suitable to achieve greater than 95% conversion of both the alkene and 3,4-di-(normal-alkyl)phenol within a 3 hour reaction time period provided that the reaction temperature and the catalyst loading are appropriately high. For example, in the case of propylene at about 120° C. to about 155° C., a suitable pressure is about 10 psig to about 50 psig (170 kPa to 446 kPa).

In addition to the alkylation of 3,4-di-(normal-alkyl)phenols of Structure III, the same catalyst may also be used to transform co-products of the alkylation process, for example other mono-(secondary-alkyl)phenol isomers of Structures IV and V and di-(secondary-alkyl)phenols of Structures VI and VII, to the desired product of Structure II. In these co-products, one or more secondary-alkyl groups, introduced by alkylation with the alkene, are connected to the 3,4-di-(normal-alkyl)phenol aromatic ring in a different position than that intended in Structure II. In Structures IV, V, VI, and VII, $R^1$ is selected from the group consisting of unsubstituted phenyl; phenyl substituted with one or more linear or branched $C_1$ to $C_6$ alkyl groups; and linear or branched $C_1$ to $C_9$ alkyl groups; $R^2$ is selected from the group consisting of linear or branched $C_1$ to $C_{14}$ alkyl groups; and $R^3$ and $R^4$ are independently selected from the group consisting of hydrogen and linear or branched $C_1$ to $C_{16}$ alkyl groups.

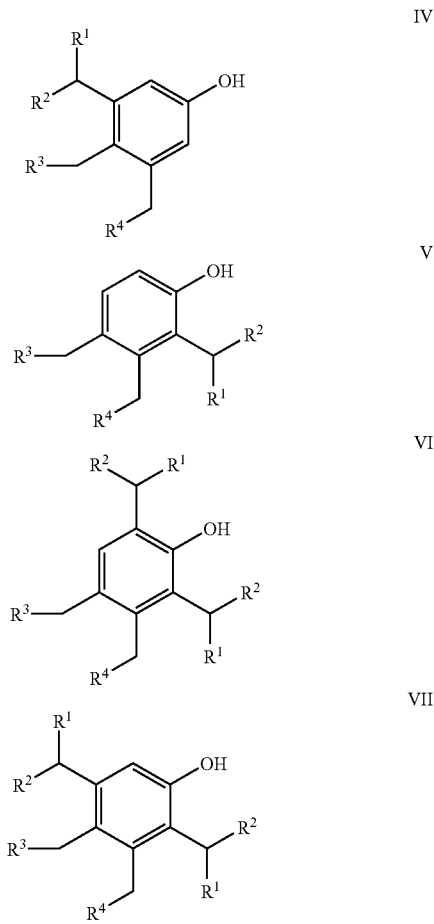

Transforming at least a portion of such co-products to the desired 2-secondary-alkyl-4,5-di-(normal-alkyl)phenol of Structure II occurs through a combination of transalkylation and isomerization of the co-products and improves yield to the desired product, beyond what may be achieved by the alkylation reaction alone. This process step can be conducted at the same time as the alkylation reaction or at a later point in time, in the same vessel or in a separate vessel. The transalkylation and isomerization reactions are conducted at a reaction temperature equal to or greater than the initial temperature for reaction of the alkene and 3,4-di-(normal-alkyl)phenols of Structure III, but preferably below temperatures which are detrimental to the stability of the catalyst. For example, the transalkylation and isomerization reactions can be performed at a temperature range of about 120° C. to about 175° C., for example from about 120° C. to about 155° C., or for example from about 150° C. to about 175° C., or from about 160° C. to about 170° C. Optionally, the transalkylation and isomerization reactions are conducted in the presence of the alkene and the 3,4-di-(normal-alkyl)phenol of Structure III. If the rates of transalkylation and isomerization are slow, an increased catalyst loading, an increased residence time for contact with the catalyst, or a combination thereof for batch and continuous operation can improve productivity significantly. Methods to determine specific operation parameters for transalkylations and isomerizations are known to those skilled in the art. Under appropriate reaction conditions for this transformation, for example an adequate catalyst, catalyst loading, residence time, and temperature, the reaction mixture after heating can comprise predominantly the desired 2-secondary-alkyl-4,5-di-(normal-alkyl)phenol of Structure II.

When compared to other catalysts such as aluminosilicates, sulfuric acid, or macroreticular resins with similar acid capacity but a different surface area and/or different distribution of the surface area in pores with a pore diameter in the range from 0.009 µm to 0.027 µm, an advantage of the catalyst of this invention is its ability to achieve alkene and 3,4-di-(normal-alkyl)phenol conversions of greater than or equal to about 95% at selectivities to 2-secondary-alkyl-3,4-di-(normal-alkyl)phenols of 70% or higher in a relatively short period of time, at a relatively low pressure and temperature, and at roughly a 1:1 feed molar ratio of alkene:3,4-di-(normal-alkyl)phenol. It is important that the catalyst maintain its stability at temperatures above 120° C. in order to sustain high activity over the period of its expected lifetime, allowing for commercially useful conversion rates, in particular with respect to the alkylation of 3,4-di-(normal-alkyl)phenols with propylene.

Upon performing the 3,4-di-(normal-alkyl)phenol alkylation with the alkene, and the transalkylation and isomerization reactions, a reaction product mixture is obtained. Processing of the reaction product mixture by the methods described wherein may be performed in batch, semi-batch, and continuous modes of operation. At least a portion of the heterogeneous acid catalyst can be separated from the reaction product mixture, for example by filtration or decantation, to produce a catalyst-depleted product mixture comprising a 2-secondary-alkyl-4,5-di-(normal-alkyl)phenol of Structure II. The separated heterogeneous acid catalyst may be reused for the alkylation reaction, transalkylation and isomerization reaction, or combinations thereof. This catalyst-depleted product mixture can optionally further comprise at least one compound of Structures IV through VII, alkene, 3,4-di-(normal-alkyl)phenol, solvent, or any combinations thereof. At least a portion of the 2-secondary-alkyl-4,5-di-(normal-alkyl)phenol can be separated from the catalyst-depleted product mixture by a variety of methods. For example, for 2-iso-propyl-4,5-dimethylphenol, the separation can be accomplished by fractional crystallization of at least a portion of this phenol product from the catalyst-depleted product mixture. The high selectivity to 2-iso-propyl-4,5-dimethylphenol achieved with the present invention helps enable this separation method. The appropriate choice of solvent and temperature are other important parameters. The mother liquor from the fractional crystallization step, that is now depleted of the desired 2-iso-propyl-4,5-dimethylphenol, may then be further processed, for example by distillation to recover a second fraction of the 2-iso-propyl-4,5-dimethylphenol present in the original catalyst-depleted product mixture. The 2-iso-propyl-4,5-dimethylphenol in this second fraction may be further purified in additional distillation or crystallization steps, optionally in the presence of the 2-iso-propyl-4,5-dimethylphenol recovered in the fractional crystallization step. Alternatively, the catalyst-depleted product mixture can bypass the fractional crystallization step and be sent directly to at least one fractional distillation step to obtain at least one fraction enriched in 2-iso-propyl-4,5-dimethylphenol. At least one fraction enriched in 2-iso-propyl-4,5-dimethylphenol may be further purified by additional distillation or crystallization steps.

In addition to at least one fraction enriched in 2-iso-propyl-4,5-dimethylphenol, additional fractions may be recovered during the distillation of the mother liquor from the fractional crystallization step or distillation of the catalyst-depleted product mixture as described above. For example, propylene and 3,4-dimethylphenol reactants may be recovered as lower-boiling fractions. 3-Iso-propyl-4,5-dimethylphenol and 2-iso-propyl-3,4-dimethylphenol isomers (Structures IV and V) may be recovered as close-boiling fractions. 2,6-Di(iso-propyl)-3,4-dimethylphenol and 2,5-di(iso-propyl)-3,4-dimethylphenol isomers (Structures VI and VII) may be recovered as higher-boiling fractions. If a solvent is utilized in the 2-iso-propyl-4,5-dimethylphenol manufacturing process, a solvent-enriched fraction may also be recovered by fractional distillation. In this discussion, the terms lower-boiling, close-boiling, and higher boiling are relative to the boiling point of the 2-secondary-alkyl-4,5-di(normal-alkyl)phenol at the chosen distillation conditions.

Optionally, the separated fractions can be recycled to the process by introducing at least a portion of one or more fractions into at least one of the process steps of 3,4-di-(normal-alkyl)phenol alkylation, transalkylation and isomerization, and crystallization. For example, a reactant fraction may be introduced into the reaction step for 3,4-di-(normal-alkyl)phenol alkylation and the mother liquor from fraction crystallization of 2-iso-propyl-4,5-dimethylphenol, fractions comprising compounds of Structures IV and V, fractions comprising compounds of Structures VI and VII, and a solvent fraction may be introduced into one or more reaction steps comprising 3,4-di-(normal-alkyl)phenol alkylation and transalkylation and isomerization. Alternatively, the reaction steps may be operated without added solvent but combine the catalyst-depleted product mixture with a solvent fraction.

Recovery and recycle of these fractions to the synthesis process for contact with the catalyst at the appropriate reaction conditions can allow alkene, 3,4-di-(normal-alkyl)phenol, and the compounds of Structures IV, V, VI, and VII to be converted to additional quantities of the desired 2-secondary-alkyl-4,5-di-(normal-alkyl)phenol of Structure II. In doing so with the present invention, it is anticipated that the conversion of 3,4-di-(normal-alkyl)phenol fed to the synthesis process may exceed 99% and the chemical yield of 2-secondary-alkyl-4,5-di-(normal-alkyl)phenol from 3,4-di-(normal-alkyl)phenol may exceed, for example 80%, for example 90%.

Optionally, at least a portion of one or more fractions can be purged from the process, for example to limit the build-up of impurities that make their way into the 2-secondary-alkyl-4,5-di-(normal-alkyl)phenol product and interfere in subsequent process steps, or for example, the build-up of higher-boiling compounds that displace reactor volume available for reactants, catalyst, and the 2-secondary-alkyl-4,5-di-(normal-alkyl)phenol product.

Oxidative coupling of a compound selected from a member of the group represented by Structure II can be used to synthesize a compound selected from a member of the group represented by Structure I, as described in the published U.S. Patent Application 2003/0100802, which is incorporated herein by reference. Compounds of Structure I can be useful starting materials in the synthesis of monodentate or bidentate organophosphorus compounds, for example phosphites, phosphinites, and phosphonites. Such organophosphorus compounds can be useful in catalytic processes, for example hydrocyanation or hydroformylation of reactants such as 1,3- butadiene, unsaturated olefins, ethylenically unsaturated nitriles, and ethylenically unsaturated esters.

Compounds of Structure I can be made by a process which comprises contacting a 3,4-di-(normal-alkyl)phenol of Structure III with an alkene containing 3 to 16 carbon atoms, a catalyst as described above, and optionally a solvent, at a first temperature in the range of about 70° C. to about 170° C. to produce a first reaction mixture comprising a 2-secondary-alkyl-4,5-di-(normal-alkyl)phenol of Structure II. The first reaction mixture is then heated at a second temperature, in the range of about 120° C. to about 175° C., which is greater than or equal to the first temperature, in the presence of the catalyst, and optionally in the presence of a solvent, to produce a second reaction mixture comprising predominantly the 2-secondary-alkyl-4,5-di-(normal-alkyl)phenol of Structure II. The 2-secondary-alkyl-4,5-di-(normal-alkyl)phenol of Structure II is then oxidatively coupled to produce a compound of Structure I. Optionally, at least a portion of the 2-secondary-alkyl-4,5-di-(normal-alkylphenol of Structure II can be isolated from the second reaction mixture prior to performing the oxidative coupling step.

Substituted phenols such as those represented by Structure II can be oxidatively coupled to make the corresponding substituted biphenols of Structure I by a variety of oxidizing agents, such as nitric acid or ferric chloride, or by using a combination of a transition metal catalyst and an oxidizing agent such as persulfate anion or oxygen. Published Patent Application US 2003/0100802 discloses a process for oxidatively coupling substituted phenols, for example 2-secondary-alkyl-4,5-di-(normal-alkyl)phenols of Structure II. The process comprises oxidatively coupling the substituted phenol in the presence of a molecular oxygen-containing gas and a copper diamine catalyst.

Preparation of a Copper Diamine Catalyst is Described in Tetrahedron Letters, 1994, 35, 7983. A copper halide, such as CuCl, CuBr, CuI, or $CuCl_2$, is added to a mixture of alcohol, such as methanol, and water and the diamine is slowly added. After the addition of the diamine, air is sparged through the mixture with vigorous stirring. The catalyst precipitates and is filtered. Examples of useful diamines include N,N,N',N'-tetramethyl-1,2-ethylenediamine, N,N,N',N'-tetraethyl-1,3-propanediamine, and N,N,N',N'-tetraethylmethanediamine. Alternatively, the catalyst can be prepared in situ by contacting the copper halide and the diamine in the solvent for the coupling reaction.

The oxidative coupling can be carried out by contacting the phenol with a copper complex of a diamine in an inert, preferably aprotic solvent such as dichloromethane, toluene, chlorobenzene, or saturated hydrocarbon, preferably one having a flash-point higher than the reaction temperature, at a temperature between 5° C. and 100° C., for example around 30° C. The product is generally isolated by dilution with a saturated hydrocarbon solvent, filtration, and optionally purified by washing with aqueous mineral acid or a copper-sequestering reagent such as the sodium salt of ethylenediaminetatraacetic acid (EDTA). The product biphenol may optionally be purified by recrystallization.

Substituted biphenols of general Structure I can be used to produce bidentate phosphite compounds, as described, for example, in U.S. Pat. Nos. 5,235,113; 6,031,120; and 6,069,267. Bidentate phosphite compounds have been shown to be useful in the hydrocyanation of monoolefinic and diolefinic compounds, as well as for the isomerization of non-conjugated 2-alkyl-3-monoalkenenitriles to 3- and/or 4-monoalkenenitriles. See, for example, U.S. Pat. Nos. 5,512,695 and 5,512,696. Bidentate phosphite ligands have also been shown to be useful in olefin hydroformylation reactions, as disclosed, for example in U.S. Pat. No. 5,235,113.

EXAMPLES

For each commercial catalyst type used for the phenol alkylation experiments (Amberlyst™ 35, Amberlyst™ 36, and Dowex™ DR-2030) catalyst samples were taken from the same manufactured lot. Catalyst surface areas and pore size distributions for these catalyst lots were derived from mercury intrusion porosimetry data using an AutoPore 9400 Series porosimeter from the Micromeritics® Instrument Corporation. Results are graphically illustrated in FIG. 1. Pore size distributions are given as $\delta V$ over $<D>$ plots where $\delta V$ is the incremental intrusion volume of the mercury in a porosimeter in cubic centimeters ($cm^3$)/gram (g) and $<D>$ is the mean pore diameter. D is the diameter of a pore calculated from the pressure p applied to the sample given by the equation $(4\gamma \cos \theta)/p$; wherein $\gamma$ is the surface tension of mercury (474 dynes/cm) and $\theta$ is the contact angle between mercury and the catalyst surface. Values $\delta V$ are corrected for compressibility. The incremental surface area $\delta SA$ is calculated based upon the standard cylindrical model with $\delta SA = 4\delta V/<D>$. The acid capacity [equivalents/kilogram (kg) resin] was determined by standard acid-base titration techniques and agreed with the manufacturer's data for each catalyst type.

Table 1 tabulates the surface area, average pore diameter, average pore size, and acid capacity of the macroreticular ion exchange resin catalysts used in Examples 1 to 23. Table 2 tabulates the surface area and surface area distribution (given in parentheses as a percentage of the total surface area) in three pore size ranges of the macroreticular ion exchange resin catalysts used in Examples 1 to 23.

TABLE 1

Characteristic Properties of Macroreticular Ion Exchange Resin Catalysts Used in Examples 1 to 23.

| | Surface Area* $[m^2/g]$ | Average Pore Size from 0.0053 μm to 0.5 μm* [μm] | Acid Capacity [equiv./kg] |
| --- | --- | --- | --- |
| Amberlyst™ 36 | 14.1 | 0.014 | 5.4 |
| Amberlyst™ 35 | 56 | 0.022 | 5.0 |
| Dowex™ DR-2030 | 44.5 | 0.032 | 4.7 |

*as determined by mercury intrusion porosimetry.

TABLE 2

Surface area $[m^2/g]$ and Surface Area Distribution (given in the parentheses as percent of the total surface area) in the Pore Size Ranges S, M, and L of Macroreticular Ion Exchange Resin Catalysts Used in Examples 1 to 23, as Measured by Mercury Intrusion Porosimetry.

| | Pore Size Range | | |
| --- | --- | --- | --- |
| | S | M | L |
| Pore Diameter | 0.003-0.009 μm | 0.009-0.027 μm | 0.027-0.109 μm |
| Amberlyst™ 36 | 1.7 (12%) | 12.1 (85%) | 0.3 (2%) |
| Amberlyst™ 35 | 3.3 (6%) | 46.7 (83%) | 5.9 (11%) |
| Dowex™ DR-2030 | 2.3 (5%) | 14.9 (33%) | 27.1 (61%) |

The results obtained by mercury intrusion porosimetry measurements show how different the pore size distributions of the three catalysts are and reveal not only that the surface area of Amberlyst™ 36 is less than 50% of the manufacturer's reported value by nitrogen BET, but also that the average pore size is significantly lower as well. According to mercury intrusion porosimetry, Amberlyst™ 35 provides the overall largest surface area and exposes more than 80% of its surface area in the medium pore size interval (M) ranging from 0.009 μm to 0.027 μm (from 90 Å to 270 Å). In contrast, Dowex™ DR-2030 shows only about 30% of the active surface area in the medium pore size range (M) with over 60% of the surface area distributed within the larger pore size interval (L) ranging from 0.027 μm to 0.109 μm (from 270 Å to 1090 Å).

Examples 1 to 19

A general description of 3,4-dimethylphenol alkylation experiments with propylene catalyzed by strongly acidic macroreticular ion exchange resins containing sulfonic acid groups is provided below. Catalysts Amberlyst™ 35 DRY and Amberlyst™ 36 DRY from the Rohm and as Company and Dowex™ DR-2030 (dry) from the Dow Chemical Company were received as dry catalysts and further dried prior to use by heating about 50 gram portions of the catalyst beads under vacuum (200 torr, 26.7 kPa) at 120° C. until constant weight was achieved.

3,4-Dimethylphenol, obtained from Sigma-Aldrich (99% purity) and from Merisol (as pure 3,4-xylenol), was dried and purified by distillation prior to use. A cylinder of propylene was obtained from a commercial vendor. The amount of propylene delivered to the reaction vessel in 3,4-dimethylphenol alkylation experiments can be determined from cylinder weight measurements made with an analytical balance. Chemical- or polymer-grade propylene is suitable for use in the present invention.

A 1000 mL stirred autoclave was charged with 500 grams of 3,4-dimethylphenol (4 moles) and the pre-determined amount of catalyst, as listed in Tables 3 and 4. The autoclave was evacuated to 200 torr (26.7 kPa) and heated to 135° C. prior to adding propylene. During all experiments, the stirring impeller speed was kept constant at 1000 revolutions per minute (rpm). Propylene was added continuously maintaining a pressure of 40 psig (380 kPa) until 176 grams of propylene (4 moles) was consumed. Subsequently, the propylene supply was disconnected and the reaction mixture was heated at 140° C. for an additional 180 minutes (min) to complete the subsequent transalkylation and isomerization reactions. The final reaction product distribution was determined by gas chromatography (GC) and quantified using a calibrated GC method. Results are given in Tables 3 and 4 and FIG. 2. Yield refers to the moles of 2-iso-propyl-4,5-dimethylphenol IIa in the product mixture relative to moles of 3,4-dimethylphenol charged, conversion (CONV) refers to the mole fraction of the starting material 3,4-dimethylphenol IIIa converted, and selectivity (SEL) refers to the mole fraction of converted 3,4-dimethylphenol to 2-iso-propyl-4,5-dimethylphenol. The remainder of the product mixture comprised other phenol co-products like those shown in Structures IV to VII where $R^1$ and $R^2$ are methyl and $R^3$ and $R^4$ are hydrogen.

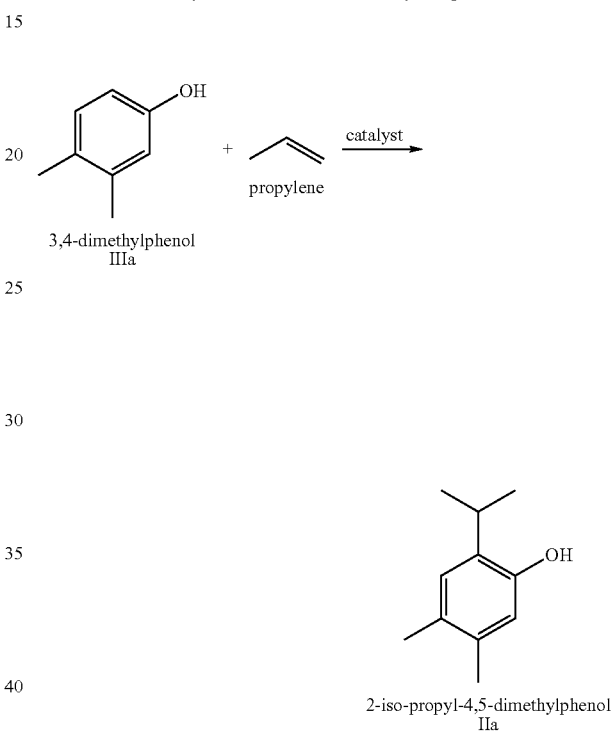

TABLE 3

Examples 1 to 10. Results for the Alkylation of 3,4-Dimethylphenol with Propylene Under Identical Conditions Using 2 wt % of Macroreticular Ion Exchange Resins with Different Surface Area Distribution in the Pore Size Range M from Pore Diameters 0.009 μm to 0.027 μm and Different Total Surface Areas as Described in Table 1 and Table 2.

| Example | Catalyst [2 wt %] | Propylene Consumption Rate [g/min] | Total Reaction Time [min]* | Yield [%] | CONV [%] | SEL [%] | Relative** Productivity |
|---|---|---|---|---|---|---|---|
| 1 | Amberlyst ™ 36 | 0.55 | 779 | 69.1 | 96.5 | 71.6 | 32.2 |
| 2 | Amberlyst ™ 36 | 0.52 | 735 | 59.0 | 92.0 | 64.1 | 29.2 |
| 3 | Amberlyst ™ 36 | 0.53 | 745 | 61.0 | 94.0 | 65.0 | 29.8 |
| 4 | Amberlyst ™ 35 | 1.96 | 267 | 72.3 | 96.7 | 74.8 | 98.4 |
| 5 | Amberlyst ™ 35 | 2.58 | 257 | 70.7 | 97.5 | 72.5 | 100.0 |
| 6 | Amberlyst ™ 35 | 2.04 | 268 | 70.5 | 97.7 | 72.2 | 95.6 |
| 7 | Amberlyst ™ 35 | 2.1 | 265 | 69.8 | 97.7 | 71.4 | 95.7 |
| 8 | Dowex ™ DR-2030 | 1.41 | 331 | 61.0 | 92.8 | 65.8 | 67.0 |
| 9 | Dowex ™ DR-2030 | 2.06 | 276 | 50.0 | 92.5 | 53.8 | 65.9 |
| 10 | Dowex ™ DR-2030 | 1.7 | 286 | 44.0 | 90.0 | 49.3 | 55.9 |

*Time until 176 grams of propylene was consumed plus 180 additional minutes heating for transalkylation and isomerization.
**Amount of 2-iso-propyl-4,5-dimethylphenol IIa produced/minute after total reaction time. Actual productivity of Amberlyst ™ 35 was higher since equilibrium concentrations are reached within less than 180 minutes under these conditions.

TABLE 4

Examples 11 to 19. Rate of Reaction (Given as Average Initial Propylene Consumption Rate) and Relative Acidity for the Alkylation of 3,4-Dimethylphenol with Propylene Under Identical Conditions Using Different Amounts of Catalyst.

| Example | Catalyst | Catalyst Amount* | Propylene Consumption Rate [g/min] | Relative Acidity |
|---|---|---|---|---|
| 11 | Amberlyst™ 36 | 1% | 0.44 | 0.7 |
| 12 | Amberlyst™ 36 | 2% | 0.54 | 1.5 |
| 13 | Amberlyst™ 36 | 5% | 1.87 | 3.7 |
| 14 | Amberlyst™ 36 | 8% | 2.34 | 5.8 |
| 15 | Amberlyst™ 36 | 16% | 3.65 | 11.7 |
| 16 | Amberlyst™ 35 | 1% | 1.18 | 2.77 |
| 17 | Amberlyst™ 35 | 2% | 2.05 | 5.5 |
| 18 | Amberlyst™ 35 | 4% | 3.27 | 11.1 |
| 19 | Dowex™ DR-2030 | 2% | 2 | 4.1 |

*Weight fraction with respect to starting material 3,4-dimethylphenol (IIIa), given as a percentage.

These data show that high reaction productivity for the alkylation of 3,4-di-(normal-alkyl)phenols of Structure III, such as 3,4-dimethylphenol, with alkenes at moderate temperatures to give 2-secondary-alkyl-4,5-di-(normal-alkyl) phenols of the general Structure II, such as 2-iso-propyl-4,5-dimethylphenol, can be achieved when a macroreticular cation exchange resin containing sulfonic acid groups and having an acid capacity of at least 4 equivalents acid per kilogram is used as catalyst. The Examples using Amberlyst™ 35, which has a surface area greater than about 40 m²/g and at least about 70%, for example at least about 75%, or for example at least about 80%, of the surface area in pores having a pore diameter from 0.009 μm to 0.027 μm (from 90 Å to 270 Å), show significantly increased selectivity to 2-secondary-alkyl-4,5-di-(normal-alkyl)phenols and reaction productivity.

While not wishing to be bound by theory, it appears that if the amount of active acid sites in pores of adequate size is directly proportional to the reaction rate of propylene consumption, Amberlyst™ 36 catalyst would be expected to show activity similar to that of Amberlyst™ 35 if a 4-5 fold amount of Amberlyst™ 36 is used. For simplicity of comparison, the relative acid strength for the catalyst loading (relative acidity) in Table 4 was calculated by multiplying the amount of catalyst (as a weight fraction with respect to the 3,4-dimethylphenol starting material) with the acid capacity and the surface area by mercury intrusion porosimetry. FIG. 3 graphically illustrates the relative acidity as a function of the initial propylene consumption rate, and suggests a linear relationship between the rate of propylene consumption and the amount of accessible acid sites in catalyst pores above an average diameter of 54 Å, the lower limit of mercury intrusion porosimetry. The difference in selectivity and productivity for Dowex™ DR-2030 compared to Amberlyst™ 35 may be explained by the different pore size distributions.

Example 20

This Example shows the sustained production of 2-iso-propyl-4,5-dimethylphenol in the presence of 2 wt % recycled Amberlyst™ 35 at 135-140° C. in a semi-continuous fashion. The results demonstrate that the catalyst can be reused multiple times under these reaction conditions without significant loss of activity.

Example 20 was conducted in the manner described in Example 1, except that Amberlyst™ 35 was used as catalyst. After performing the transalkylation and isomerization reaction step, the catalyst was allowed to settle and the product was decanted from the catalyst. The autoclave containing the catalyst was recharged with another batch of 500 grams 3,4-dimethylphenol and reacted with another batch of 176 grams propylene in the same fashion. This procedure was repeated until a total of 2500 grams 3,4-dimethylphenol and 880 grams propylene were consumed using the same 10 gram charge of Amberlyst™ 35. Results shown in Table 5 indicate a catalyst usage of less than 0.4% at the high productivity regime of the present invention.

TABLE 5

Results for the Semi-Continuous Alkylation of 3,4-Dimethylphenol (Example 20) with Propylene Using Amberlyst™ 35 Catalyst.

| Run | Relative Rate of Propylene Consumption | 2-Iso-propyl-4,5-Dimethylphenol Yield (%) | 3,4-Dimethylphenol Conversion (%) | Cumulative Catalyst Usage* |
|---|---|---|---|---|
| 1 | 0.85 | 75 | 97 | 2% |
| 2 | 1.26 | 72 | 96 | 1% |
| 3 | 0.98 | 73 | 95 | 0.7% |
| 4 | 0.95 | 76 | 94 | 0.5% |
| 5** | 0.66 | 73 | 96 | 0.4% |

*Initial Amberlyst™ 35 catalyst charge (grams)/cumulative weight of 3,4-dimethylphenol (grams) processed within the autoclave.
**Unexpected pressure drop during experiment due to empty propylene cylinder.

Example 21

In addition to 2-iso-propyl-4,5-dimethylphenol IIa, the reaction product mixtures from Examples 1 to 20 also comprise various quantities of 3,4-dimethylphenol IIIa and co-products, for example the mono-(iso-propyl)phenol isomers IVa and Va and di-(iso-propyl)phenols VIa and VIIa shown below. The mono-(iso-propyl)phenol isomers result from monoalkylation of the 3,4-dimethylphenol starting material at an undesired position on the aromatic ring. The di-(iso-propyl)phenols result from alkylation of a mono-(iso-propyl) phenol isomer.

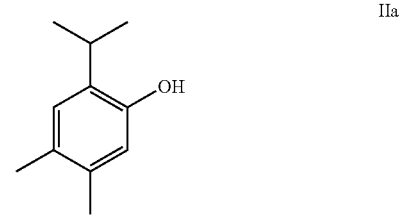

IIa

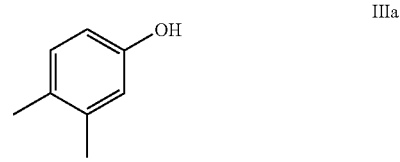

IIIa

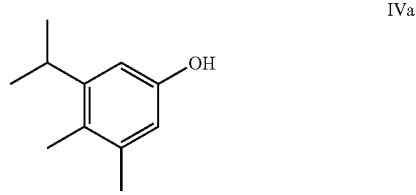

IVa

Va

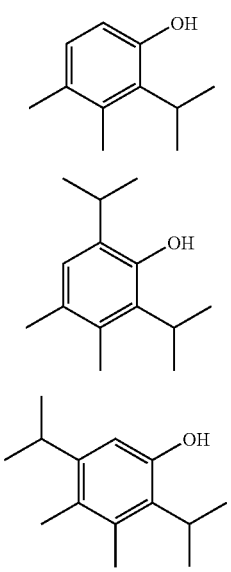

VIa

VIIa

Reaction product mixtures from several larger-scale propylation experiments each using 1-2 kilograms of 3,4-dimethylphenol are obtained similarly to those described in Examples 1 to 20 or by using a different heterogeneous acid catalyst, for example Amberlyst™ 15 or phosphotungstic acid hydrate. Such reaction product mixtures are combined for a total of about 15 liters. The catalyst is separated from the reaction product mixture to limit conversion of IIa, for example, to propylene and 3,4-dimethylphenol. The mixture is then pumped into a semi-continuous, vacuum single-stage still operating at a head pressure of about 30 torr (4 kPa). An overhead stream enriched in the lower-boiling materials comprising iso-propylcresol isomers [(($CH_3)_2CH)(CH_3)C_6H_3OH$], IIa, IIIa, IVa, Va, and VIa is obtained from the still with a head temperature of about 148° C. and a pot temperature of about 149° C. A total of about 14 liters of the overhead stream is collected. The material remaining in the pot, about 1 liter in volume, is enriched in the di-(iso-propyl)phenols VIa and VIIa.

About 12 liters of the overhead product stream are then further refined in a second distillation in a 2 inch (5 cm) internal diameter 45 tray Oldershaw column equipped with a vapor-type splitter [head pressure 60 torr (8 kPa)]. The pot temperature ranges from 174° C. to 199° C., and the head temperature ranges from 143° C. to 167° C. Fore-cut fractions comprising iso-propylcresol isomers, IIa, IIIa, and Va are removed at a 4:1 reflux ratio and are then finished at a 10:1 reflux ratio. The major fraction comprising IIa, IVa, Va, and VIa is removed at a 3:1 reflux ratio and then finished at a 5:1 reflux ratio. Collection of the major fraction is stopped when the IIa content in the distillate falls below about 93%. The purity of IIa in the major fraction is about 97% with a 50% one pass yield.

This distillation example shows that the co-product 2-iso-propyl-3,4-dimethylphenol Va is present in every distillation fraction comprising the desired product IIa so it will be challenging to separate from IIa by distillation. In the case where a mixture of Va and IIa is subsequently oxidatively coupled to make the 2,2'-biphenol of Structure Ia, the presence of Va in the refined product IIa can also result in the formation of an additional 2,2'-biphenol co-product VIIIa having general structure VIII that is anticipated to be difficult to separate from the desired 2,2'-biphenol Ia of general Structure I. Likewise, it may be better to operate the propylation reaction and transalkylation and isomerizations reaction at high 3,4-dimethylphenol conversion than to increase conversion by returning the lower-boiling fraction comprising 3,4-dimethylphenol and iso-propylcresol isomers to the propylation reaction. This distillation example also shows that the co-products IVa and VIa are close-boilers to IIa and require adequate reflux for good separation.

Ia

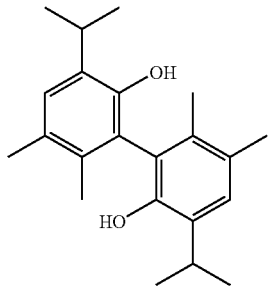

VIIIa

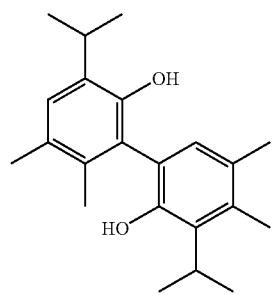

VIII

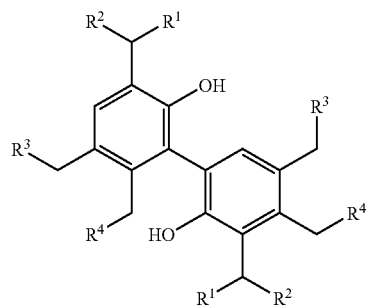

Example 22

One method to alleviate the problem of Va co-distilling with IIa is to utilize the transalkylation and isomerization reaction procedure described above to reduce the distribution of undesired co-products, comprising Va, and to increase conversion to the desired product.

To demonstrate isolation of the desired material via distillation after 3,4-dimethylphenol propylation, then transalkylation and isomerization reactions, a reaction product mixture was generated from 1005 g of 3,4-dimethylphenol and 492 g of propylene using 2 wt % Amberlyst™ 35 catalyst. No solvent was used. The reaction was performed in a 1000 mL stirred autoclave with 40 psig (377 kPa) dynamic propylene pressure at 155° C., followed by transalkylation and isomerization at 165° C. until the product distribution reached the targeted amount of IIa (74-75% by GC area percent). After transalkylation and isomerization, the reaction mixture contained, on a weight percentage basis, 75.1% desired product IIa, 12.7% IVa, 5.9% VIa, 2.7% 3,4-dimethylphenol starting material IIIa, 1.5% VIIa, 0.5% Va, 0.6% iso-propylcresol isomers, and 0.9% unidentified material. The concentration of Va decreases from about 4% after the propylation step to about 0.5% after the transalkylation and isomerization step at a 3,4-dimethylphenol conversion of greater than 97%.

The reaction product mixture was then filtered at about 50° C. through a coarsely fritted funnel to separate the catalyst from a catalyst-depleted product mixture. This product mixture can be distilled in a batch or continuous manner. The catalyst-depleted product mixture was then transferred into a distillation unit consisting of a 25-plate 1" Oldershaw column with vapor splitter (approximately 15 theoretical stages). Fractional distillation was performed under a constant pressure of 50 torr (6.7 kPa) and with a condenser temperature of about 80° C. over a net time period of 17 hours. Distillation conditions are presented in Table 6. 3,4-Dimethylphenol and low boiling by-products, including iso-propylcresol isomers, were removed at a 5:1 to 50:1 reflux ratio. Product fractions of IIa at a purity of greater than 95% by GC were collected at a 2:1 reflux ratio. Fractions IC1 to HC9 were combined resulting in an average purity of 96% IIa. Use of higher reflux ratios would enable higher purities of IIa to be achieved, for example greater than 98%. Table 7 summarizes the distillate characterization by GC analysis.

The high-boiling material remaining in the distillation unit, the distillation tails, was about 11 wt % of the initial charge to the distillation unit and contained, on a GC area percentage basis, 68% IVa, 9.4% VIa, 10.8% VIIa, and less than 1% IIa.

At least a portion of the distillation tails is purged from the process to remove di(iso-propyl)cresols and various diarylether compounds. At least a portion of the distillation tails in contact with catalyst undergoes transalkylation and isomerization to produce additional IIa. At least a portion of the distillate fractions, for example distillate fractions FC1 to FC6, is purged from the process to remove iso-propylcresols. At least a portion of the distillate fractions, for example distillate fractions FC1 to FC6 and HC10 and HC11, is recycled to the 3,4-dimethylphenol propylation or transalkylation and isomerization steps to increase yield to IIa.

TABLE 6

Distillation of Catalyst-Depleted Reaction Product (Example 22).

| Distillate Fraction | Temp (° C.) Splitter | Temp (° C.) Pot | Reflux Ratio | Wt % of Total | IIa Purity (%) |
| --- | --- | --- | --- | --- | --- |
| FC1 | 141 | 173 | 10:1 | 4.7 | 27.5 |
| FC2 | 157 | 173 | 5:1 | 5.7 | 83.5 |
| FC3 | 160 | 174 | 5:1 | 5.7 | 90.4 |
| FC4 | 161 | 174 | 50:1 | 2.0 | 79.3 |
| FC5 | 161 | 176 | 50:1 | 1.2 | 90.3 |
| FC6 | 161 | 176 | 50:1 | 1.3 | 93.7 |
| IC1 | 161 | 176 | 50:1 | 1.1 | 95.2 |
| IC2 | 161 | 176 | 2:1 | 3.0 | 97.7 |
| HC1 | 162 | 177 | 2:1 | 5.7 | 98.2 |
| HC2 | 162 | 177 | 2:1 | 5.7 | 98.1 |
| HC3 | 162 | 177 | 2:1 | 6.4 | 97.7 |
| HC4 | 162 | 178 | 2:1 | 6.1 | 97.5 |
| HC5 | 162 | 179 | 2:1 | 6.1 | 97.3 |
| HC6 | 162 | 180 | 2:1 | 6.0 | 96.4 |
| HC7 | 163 | 181 | 2:1 | 6.1 | 94.6 |
| HC8 | 163 | 182 | 50:1 | 2.0 | 97.9 |
| HC9 | 163 | 183 | 2:1 | 6.0 | 87.3 |
| HC10 | 163 | 184 | 2:1 | 5.8 | 56.6 |
| HC11 | 170-175 | 186-190 | 2:1 | 6.4 | 16.1 |

TABLE 7

GC Analysis (Area %) of Distillate Fractions (Example 22).

| Distillate Fraction | Mass (grams) | IIIa | Iso-propylcresol Isomers | IIa | Va | IVa | VIa |
| --- | --- | --- | --- | --- | --- | --- | --- |
| FC1 | 68.37 | 42.4 | 23.69 | 27.48 | 0.28 | | |
| FC2 | 82.62 | 5.85 | 7.10 | 83.51 | 0.65 | | |
| FC3 | 82.46 | 2.52 | 4.11 | 90.40 | 0.63 | | |
| FC4 | 28.78 | 5.50 | 9.62 | 79.29 | 0.72 | | |
| FC5 | 17.86 | 1.56 | 3.30 | 90.31 | 0.79 | | |
| FC6 | 19.27 | 0.84 | 1.42 | 93.65 | 0.84 | | |
| IC1 | 15.77 | 0.52 | 0.57 | 95.23 | 0.79 | | |
| IC2 | 44.08 | | | 97.74 | 0.58 | 0.17 | 0.22 |
| HC1 | 83.36 | | | 98.22 | 0.48 | 0.28 | 0.38 |
| HC2 | 83.51 | | | 98.06 | 0.48 | 0.31 | 0.41 |
| HC3 | 93.58 | | | 97.73 | 0.46 | 0.38 | 0.52 |
| HC4 | 89.59 | | | 97.50 | 0.53 | 0.38 | 0.50 |
| HC5 | 89.25 | | | 97.31 | 0.44 | 0.57 | 0.77 |
| HC6 | 86.96 | | | 96.39 | 0.40 | 0.89 | 1.14 |
| HC7 | 88.36 | | | 94.56 | 0.38 | 1.57 | 1.90 |
| HC8 | 28.97 | | | 97.93 | 0.55 | 0.25 | 0.38 |
| HC9 | 87.46 | | | 87.34 | 0.12 | 4.15 | 4.71 |
| HC10 | 85.15 | | | 56.64 | 0.34 | 19.03 | 16.52 |
| HC11 | 93.47 | | | 16.09 | 0 | 47.97 | 25.86 |

Example 23

This Example demonstrates the use of an aliphatic hydrocarbon solvent for the propylation of 3,4-dimethylphenol and transalkylation and isomerization step. In addition, this Example demonstrates isolation of the desired product by fractional crystallization. The solvent used was ExxonMobil Chemical's ISOPAR® L, which is an "isoparaffinic", saturated hydrocarbon solvent consisting of branched and linear alkanes with a boiling point range of approximately 190-225° C. When such a solvent is used for propylation of 3,4-dimethylphenol, less formation of high-boiling and colored impurities are observed than when the propylation is performed without solvent (neat). Use of at least some solvent in a process to prepare 2-secondary-alkyl-4,5-di-(normal-alkyl) phenols can also be helpful in, for example, as a filtration aide and increasing the solubility of the alkene in the reaction mixture.

A crude reaction mixture was generated from 500 g 3,4-dimethylphenol and 195 g propylene using 125 g ISOPAR® L and 10 g of Amberlyst™ 35 catalyst. The catalyst had been previously activated by heating at 120° C. under vacuum for 12 hours. A propylene pressure of 40 psig (377 kPa) was maintained at 145° C. After 1.1 molar equivalents of propylene were absorbed at about 132 minutes of reaction, the reactor was isolated from the propylene cylinder and the temperature was raised to 150° C. and held for about 2 hours, then raised to 165° C. and held for about 3 hours for transalkylation and isomerization reactions to occur. Samples of the reaction mixture were taken after completion of the semi-batch propylation and at various stages of the transalkylation and isomerization reaction then analyzed by GC.

TABLE 8

Product Distribution and Conversion of 3,4-Dimethylphenol During Propylation and Transalkylation/Isomerization as Monitored by GC Analysis (Example 23).

| Reaction time (min) | IIIa (wt %) | Iso-propylcresol Isomers (wt %) | IIa (wt %) | Va (wt %) | IVa (wt %) | VIa (wt %) | VIIa (wt %) | CONV (%) |
|---|---|---|---|---|---|---|---|---|
| 132 | 6.5 | 0.7 | 58.2 | 4.7 | 9.8 | 13.4 | 4.7 | 91 |
| 255 | 2.1 | 1.4 | 70.3 | 0.9 | 12.4 | 9.0 | 2.4 | 97 |
| 435 | 1.3 | 1.9 | 71.6 | 0.1 | 12.4 | 7.3 | 1.8 | 98 |

The reaction mixture was a clear colorless solution with dark grey catalyst beads. The reaction mixture was filtered while hot (about 45-50° C.) using a fast filter paper and porcelain filter under about 200 torr (27 kPa) vacuum suction to separate the catalyst and to obtain the crude product solution. Filtration was rapid. In contrast to Amberlyst™ 15, the catalyst appeared structurally intact and no fine catalyst particles were observed. About 96% of the expected mass was recovered as the catalyst-depleted product mixture.

The crystallization of the desired product can be performed in a batch or continuous manner. The desired product IIa was crystallized from this product mixture by lowering the temperature of the catalyst-depleted product mixture from 45° C. to 20° C. over 1 hour, then cooling it to about 8° C. over 30 minutes and holding that temperature for 1 hour. The crystallization mixture was filtered through a coarsely fritted glass filter (80-100 microns, 200 torr, 27 kPa). Suction was applied for 2 hours to drain a major portion of the mother liquor from the crystals (384 g). The initial crop of crystals was washed with 100 g of cold ISOPAR® L to obtain the final crop (365 g). The ISOPAR® L wash was kept separate from the mother liquor. The purity of the final crystal crop obtained by this procedure was greater than 98% by quantitative GC analysis. The melting point of the solvent-free 2-iso-propyl-4,5-dimethylphenol is about 69° C.

TABLE 9

Composition of Crude Product Solution, Final Crystal Crop, and Mother Liquor as Weight Percent by GC Analysis (Example 23).

| Stream | IIIa (wt %) | Iso-propylcresol Isomers (wt %) | IIa (wt %) | Va (wt %) | IVa (wt %) | VIa (wt %) | VIIa (wt %) |
|---|---|---|---|---|---|---|---|
| Catalyst-depleted Product Mixture | 1.5 | 1.8 | 70.8 | 0.5 | 12.5 | 7.6 | 2.1 |
| Final Crystal Crop | 0 | 0.5 | 98.5 | 0 | 0.3 | 0.5 | 0 |
| Mother Liquor | 3.2 | 3.4 | 34.9 | 0.9 | 27.8 | 16.7 | 4.5 |

The yield of IIa may be increased by recycling at least a portion of the mother liquor comprising IIa, IIIa, IVa, Va, VIa, and VIIa back to one or more reaction steps comprising 3,4-dimethylphenol propylation and transalkylation and isomerization, as described above, with optional addition of 3,4-dimethylphenol, propylene, and make-up catalyst, followed by another crystallization step as described above.

At least a portion of the mother liquor may be distilled to recover an additional amount of IIa.

Example 24

IVa is the major co-product from the isomerization/transalkylation step. A mother liquor similar one described in Example 23 was vacuum distilled to obtain a distillation fraction primarily comprising only IIa and IVa with a low IIa/IVa ratio of about 0.37. It was combined with Amberlyst™ 35 (8 wt %) then heated to 160° C. for a period of 24 hours with filtered samples withdrawn at various times. GC analysis results for the samples are shown in Table 10 demonstrating IVa conversion to additional amounts of IIa that may be purified by distillation and crystallization.

TABLE 10

GC Analysis Results for Isomerization of a Mother Liquor Distillation Fraction to Produce IIa (Example 24).

| Time (Hours) | IIa (moles/L) | IVa (moles/L) | Ia (moles/L) | Other Products (moles/L) | IVa CONV (mole %) | IIa SEL (mole %) |
|---|---|---|---|---|---|---|
| 0 | 0.60 | 1.64 | 0.06 | 0.00 | 0 | 0 |
| 4 | 1.05 | 0.88 | 0.03 | 0.35 | 47 | 60 |
| 7.7 | 1.23 | 0.66 | 0.03 | 0.38 | 60 | 64 |
| 12.3 | 1.33 | 0.51 | 0.03 | 0.43 | 69 | 65 |
| 24 | 1.40 | 0.34 | 0.04 | 0.52 | 79 | 62 |

Whether the desired product is isolated from the reaction product by distillation or by crystallization, the 3,4-dimethylphenol propylation step, or more generally the 3,4-di-(normal-alkyl)phenol alkylation step which produces a first reaction mixture, can be performed in the same reaction vessel or in a separate vessel from that used for the isomerization/transalkylation reaction step which produces a second reaction mixture. When the first and second reaction mixtures are produced in the same reaction vessel, the same charge of catalyst can be used. When the first and second reaction mixtures are produced in separate reaction vessels, separate catalyst charges are used. The choice of using the same reaction vessel or separate reaction vessels for the alkylation and isomerization/transalkylation steps will depend in part on the desired productivity and other economic considerations.

Example 25

Preparation of 3,3'-di(isopropyl)-5,5',6,6'-tetramethyl-2,2'-biphenol by oxidative coupling of 2-iso-propyl-4,5-dimethylphenol purified by distillation or crystallization To a solution of 15.0 g (0.0915 mol) of 2-iso-propyl-4,5-dimethylphenol (IIa, ≧98% purity) in 15 mL of dichloromethane was added 0.75 g (3.2 mmol) of copper chlorohydroxide-TMEDA complex. The solution was stirred exposed to the air for 4 to 6 hours at ambient temperature. The mixture was stirred with 5 mL of saturated aqueous disodium EDTA for 10 minutes to decompose Cu-complexes, diluted with 80 mL of hexanes, and the hexane layer was concentrated to dryness. The crude product was crystallized from hexanes to afford two crops totaling 8.5 g of 3,3'-diisopropyl-5,5',6,6'-tetramethyl-2,2'-biphenol (VIIIa, 63% yield based on 90% conversion), $^1$H-NMR (CDCl$_3$) δ=1.24 (d, 6H, J=7 Hz), 1.87 (s, 3H), 2.26 (s, 3H), 3.26 (septet, 1H, J=7 Hz), 4.6 (s, 1H), 7.06 (s, 1H) ppm. The first crop had mp 107° C. (lit. U.S. Pat. No. 4,880,775: mp 106-107.5° C.).

Although particular embodiments of the present invention have been described in the foregoing description, it will be understood by those skilled in the art that the invention is capable of numerous modifications, substitutions and rearrangements without departing from the spirit or essential attributes of the invention. Reference should be made to the appended claims, rather than to the foregoing specification, as indicating the scope of the invention.

What is claimed is:

1. A process for making 2-secondary-alkyl-4,5-di-(normal-alkyl)phenols of Structure II, said process comprising the following steps:
   (i) contacting a 3,4-di-(normal-alkyl)phenol of Structure III with an alkene in the presence of a heterogeneous acid catalyst and optionally in the presence of a solvent at a first temperature in the range of about 70° C. to about 170° C. to produce a first reaction mixture comprising 2-secondary-alkyl-4,5-di-(normal-alkyl)phenol;

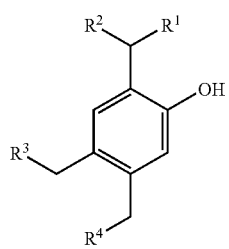

II

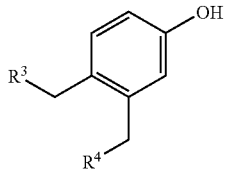

III wherein, in Structures II and III:
   $R^1$ is selected from the group consisting of unsubstituted phenyl; phenyl substituted with one or more linear or branched $C_1$ to $C_6$ alkyl groups; and linear or branched $C_1$ to $C_9$ alkyl groups;
   $R^2$ is selected from the group consisting of linear or branched $C_1$ to $C_{14}$ alkyl groups;
   $R^3$ and $R^4$ are independently selected from the group consisting of hydrogen and linear or branched $C_1$ to $C_{16}$ alkyl groups;
wherein, the alkene contains 3 to 16 carbon atoms;
wherein the heterogeneous acid catalyst is a macroreticular cation exchange resin containing sulfonic acid groups and having an acid capacity of at least 4 equivalents acid per kilogram; and
(ii) heating the first reaction mixture at a second temperature in the range of about 120° C. to about 175° C. to produce a second reaction mixture comprising predominantly 2-secondary-alkyl-4,5-di-(normal-alkyl)phenol, wherein the second temperature is greater than or equal to the first temperature.

2. The process of claim 1, wherein the solvent comprises at least one saturated aliphatic hydrocarbon.

3. The process of claim 1 further comprising (iii) separating at least a portion of the catalyst from the second reaction mixture to produce a third reaction mixture depleted in catalyst and comprising 2-secondary-alkyl-4,5-di-(normal-alkyl)phenol.

4. The process of claim 3, further comprising (iv) separating at least a portion of the 2-secondary-alkyl-4,5-di-(normal-alkyl)phenol from the third reaction mixture.

5. The process of claim 4, further comprising returning at least some of the remaining portion of the third reaction mixture to step (i) or step (ii), or to both of steps (i) and (ii).

6. The process of claim 3, further comprising (v) separating at least a portion of any 3,4-di-(normal-alkyl)phenol of Structure III from the third reaction mixture and returning at least a portion of the 3,4-di-(normal-alkyl)phenol to step (i).

7. The process of claim 3, wherein the third reaction mixture further comprises at least one di-(secondary-alkyl)phenol selected from the group consisting of compounds of Structure VI, Structure VII, and mixtures thereof,

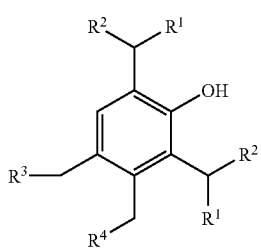

VI

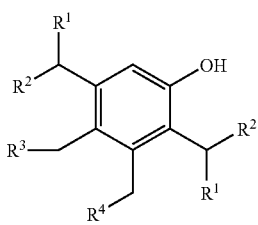

and wherein, in Structure VI and Structure VII, $R^1$ is selected from the group consisting of unsubstituted phenyl; phenyl substituted with one or more linear or branched $C_1$ to $C_6$ alkyl groups; and linear or branched $C_1$ to $C_9$ alkyl groups; $R^2$ is selected from the group consisting of linear or branched $C_1$ to $C_{14}$ alkyl groups; and $R^3$ and $R^4$ are independently selected from the group consisting of hydrogen and linear or branched $C_1$ to $C_{16}$ alkyl groups, further comprising (vi) separating at least a portion of the di-(secondary-alkyl)phenol from the third reaction mixture.

8. The process of claim 7, further comprising (vii) returning at least a portion of the di-(secondary-alkyl)phenol separated from the third reaction mixture to step (i) or (ii).

9. The process of claim 8, wherein said portion of the di-(secondary-alkyl)phenol which is separated from the third reaction mixture is returned to step (ii).

10. The process of claim 7, wherein at least a portion of the di-(secondary-alkyl)phenol which is separated from the third reaction mixture is purged from the process.

11. The process of claim 3, wherein the third reaction mixture further comprises at least one mono-(secondary-alkyl)phenol selected from the group consisting of Structure IV, Structure V, and mixtures thereof,

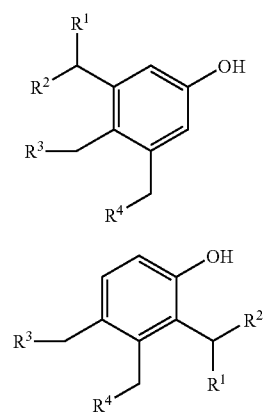

and wherein, in Structure IV and Structure V, $R^1$ is selected from the group consisting of unsubstituted phenyl; phenyl substituted with one or more linear or branched $C_1$ to $C_6$ alkyl groups; and linear or branched $C_1$ to $C_9$ alkyl groups; $R^2$ is selected from the group consisting of linear or branched $C_1$ to $C_{14}$ alkyl groups; and $R^3$ and $R^4$ are independently selected from the group consisting of hydrogen and linear or branched $C_1$ to $C_{16}$ alkyl groups, further comprising (viii) separating at least a portion of the mono-(secondary-alkyl)phenol from the third reaction mixture and returning it to step (i) or to step (ii), or a combination thereof.

12. The process of claim 4, wherein the separation is by distillation.

13. The process of claim 12, wherein the distillation provides at least one distillate fraction and a distillation tails, and wherein the process further comprises returning at least a portion of the distillate fraction to step (i) or (ii), or to both of steps (i) and (ii).

14. The process of claim 12, wherein the distillation is continuous.

15. The process of claim 12, wherein the distillation is batch.

16. The process of claim 4, wherein the separation is by crystallization.

17. The process of claim 16, wherein at least a portion of the mother liquor obtained from the crystallization is returned to step (i) or to step (ii), or to both of steps (i) and (ii).

18. The process of claim 16, wherein the crystallization is continuous.

19. The process of claim 16, wherein the crystallization is batch.

20. The process of claim 1, wherein the first reaction mixture and the second reaction mixture are produced in a batch or semi-batch manner in the same reaction vessel.

21. The process of claim 1, wherein the first reaction mixture and the second reaction mixture are produced in a continuous manner in separate reaction vessels.

22. The process of claim 1, wherein the macroreticular cation exchange resin has a surface area greater than about 40 $m^2/g$ and at least about 70% of the surface area of the macroreticular cation exchange resin is in pores with a pore diameter from 0.009 to 0.027 μm as measured by mercury intrusion porosimetry.

23. A process to improve yield in the synthesis of 2-secondary-alkyl-4,5-di-(normal-alkyl)phenols of Structure II, the process comprising:

heating to a temperature in the range of about 120° C. to about 175° C. in the presence of a heterogeneous acid catalyst a first reaction mixture comprising 2-secondary-alkyl-4,5-di-(normal-alkyl)phenol and at least one compound selected from the group consisting of compounds of Structure IV, V, VI, VII, and a mixture thereof, the first reaction mixture being obtained by alkylation of a 3,4-di-(normal-alkyl)phenol with an alkene in the presence of the heterogeneous acid catalyst, to obtain a second reaction mixture comprising 2-secondary-alkyl-4,5-di-(normal-alkyl)phenol;

wherein the yield of the 2-secondary-alkyl-4,5-di-(normal-alkyl)phenol is increased after heating the second reaction mixture;

wherein, in Structure II, IV, V, VI, and VII:

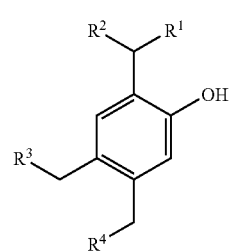

-continued

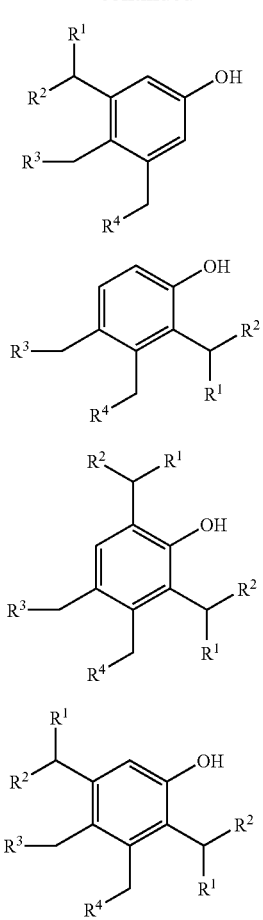

R¹ is selected from the group consisting of unsubstituted phenyl; phenyl substituted with one or more linear or branched $C_1$ to $C_6$ alkyl groups; and linear or branched $C_1$ to $C_9$ alkyl groups;

R² is selected from the group consisting of linear or branched $C_1$ to $C_{14}$ alkyl groups;

R³ and R⁴ are independently selected from the group consisting of hydrogen and linear or branched $C_1$ to $C_{16}$ alkyl groups;

wherein, the alkene contains 3 to 16 carbon atoms; and wherein the heterogeneous acid catalyst is a strongly acidic macroreticular cation exchange resin containing sulfonic acid groups and having an acid capacity of at least 4 equivalents acid per kilogram.

24. The process of claim 23, wherein the 3,4-di-(normal-alkyl)phenol is 3,4-dimethylphenol and the alkene is propylene.

25. The process of claim 23, wherein the macroreticular cation exchange resin has a surface area greater than about 40 $m^2/g$.

26. The process of claim 25, wherein at least about 70% of the surface area is in pores with a pore diameter from 0.009 to 0.027 μm as measured by mercury intrusion porosimetry.

27. A process for making a compound of Structure I, the process comprising;

(a) contacting a 3,4-di-(normal-alkyl)phenol of Structure III with an alkene in the presence of a heterogeneous acid catalyst and optionally in the presence of a solvent at a first temperature in the range of about 70° C. to about 170° C. to produce a first reaction mixture comprising a 2-secondary-alkyl-4,5-di-(normal-alkyl)phenol of Structure II;

(b) heating the first reaction mixture at a second temperature in the range of about 120° C. to about 175° C. in the presence of the heterogeneous acid catalyst, and optionally in the presence of a solvent, to produce a second reaction mixture comprising predominantly the 2-secondary-alkyl-4,5-di-(normal-alkyl)phenol of Structure II, wherein the second temperature is greater than or equal to the first temperature; and (c) performing oxidative coupling of the 2-secondary-alkyl-4,5-di-(normal-alkyl)phenol of Structure II to produce a compound of Structure I;

wherein, in Structures I, II, and III,

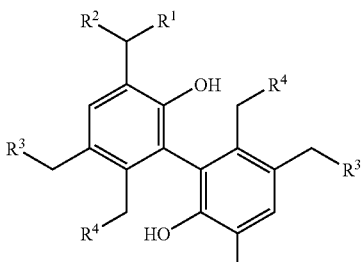

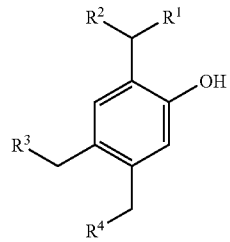

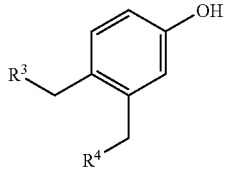

R¹ is selected from the group consisting of unsubstituted phenyl; phenyl substituted with one or more linear or branched $C_1$ to $C_6$ alkyl groups; and linear or branched $C_1$ to $C_9$ alkyl groups;

R² is selected from the group consisting of linear or branched $C_1$ to $C_{14}$ alkyl groups;

R³ and R⁴ are independently selected from the group consisting of hydrogen and linear or branched $C_1$ to $C_{16}$ alkyl groups;

wherein, the alkene contains 3 to 16 carbon atoms; and wherein the heterogeneous acid catalyst is a strongly acidic macroreticular cation exchange resin containing sulfonic acid groups and having an acid capacity of at least 4 equivalents acid per kilogram.

28. The process of claim 27, wherein the 3,4-di-(normal-alkyl)phenol is 3,4-dimethylphenol and the alkene is propylene.

29. The process of claim 27, wherein at least a portion of the 2-secondary-alkyl-4,5-di-(normal-alkyl)phenol of Structure II is isolated from the second reaction mixture prior to performing the oxidative coupling of step (c).

30. The process of claim 27, wherein the macroreticular cation exchange resin has a surface area greater than about 40 $m^2/g$.

31. The process of claim 30, wherein at least about 70% of the surface area is in pores with a pore diameter from 0.009 to 0.027 µm as measured by mercury intrusion porosimetry.

* * * * *